(12) United States Patent
Tokunaga et al.

(10) Patent No.: US 8,430,321 B2
(45) Date of Patent: Apr. 30, 2013

(54) SAMPLE ANALYZER AND REAGENT INFORMATION WRITING METHOD

(75) Inventors: Kazutoshi Tokunaga, Kakogawa (JP); Yuji Wakamiya, Kobe (JP)

(73) Assignee: Sysmex Corporation (JP)

( * ) Notice: Subject to any disclaimer, the term of this patent is extended or adjusted under 35 U.S.C. 154(b) by 0 days.

(21) Appl. No.: 13/115,707

(22) Filed: May 25, 2011

(65) Prior Publication Data

US 2011/0290890 A1 Dec. 1, 2011

(30) Foreign Application Priority Data

May 31, 2010 (JP) .................................. 2010-125379

(51) Int. Cl.
*G06F 17/00* (2006.01)
(52) U.S. Cl.
USPC ....................................... 235/487; 340/572.1
(58) Field of Classification Search .................. 235/375; 340/572.1
See application file for complete search history.

(56) References Cited

U.S. PATENT DOCUMENTS

2008/0224871 A1* 9/2008 Bolotin et al. ............. 340/572.1

FOREIGN PATENT DOCUMENTS

JP 2008-203007 A 9/2008

* cited by examiner

*Primary Examiner* — Daniel Hess
(74) *Attorney, Agent, or Firm* — Brinks Hofer Gilson & Lione

(57) ABSTRACT

The present invention is a sample analyzer for analyzing a sample by using a reagent contained in a reagent container, which includes: a reagent container holder configured to hold a reagent container to which an information storage medium is attached; an actuator configured to actuate the reagent container holder to move the reagent container held by the reagent container holder to a first position and a second position different from the first position; a reagent aspirator configured to aspirate a reagent from the reagent container when the reagent container is located at the first position; an information communication section configured to write reagent amount information regarding an amount of the reagent in the reagent container, into the information storage medium attached to the reagent container when the reagent container is located at the second position; and a controller configured to control at least the actuator and the information communication section.

16 Claims, 17 Drawing Sheets

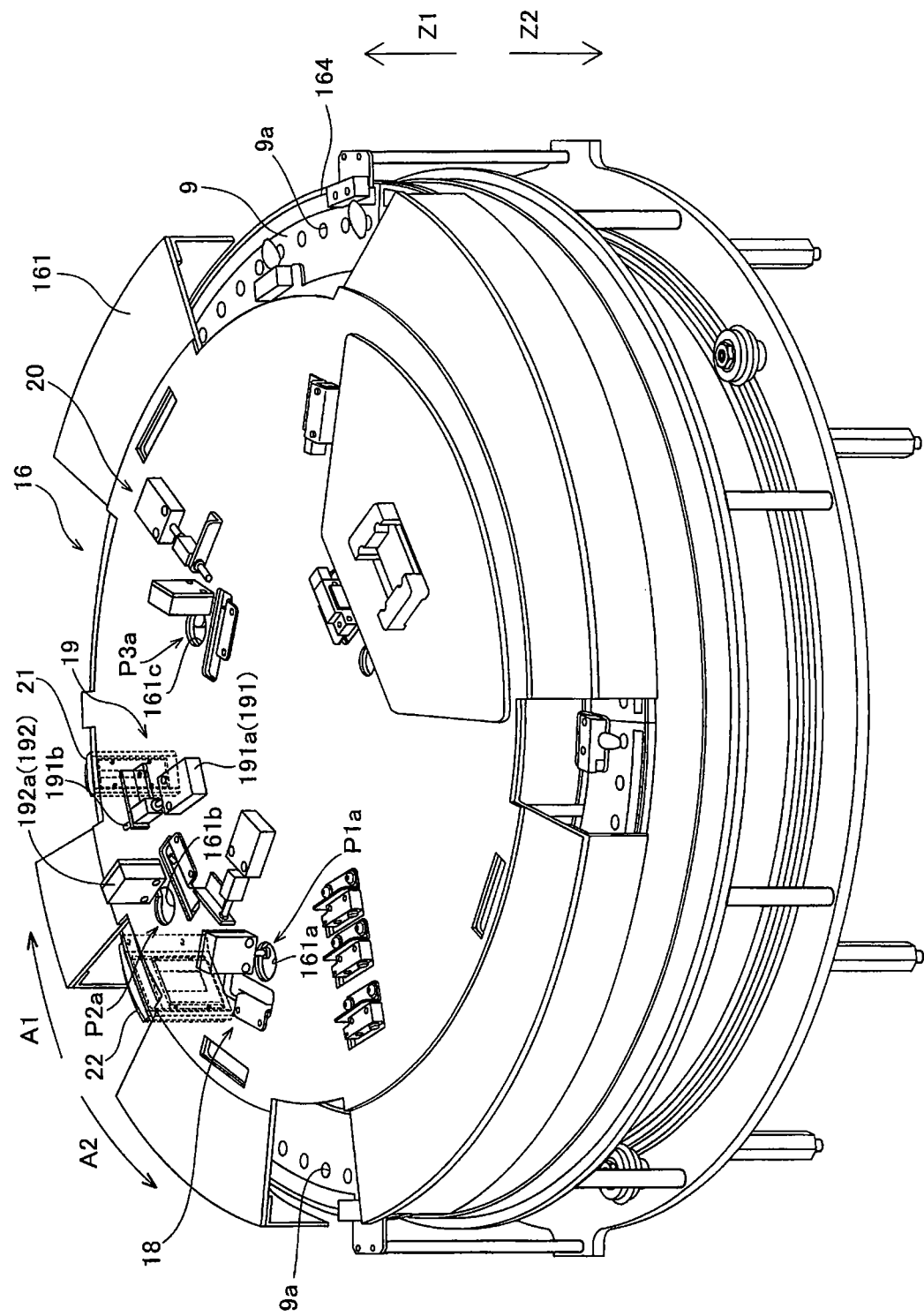
F I G. 5

SAMPLE ANALYZER AND REAGENT INFORMATION WRITING METHOD

RELATED APPLICATIONS

This application claims priority under 35 U.S.C. §119 to Japanese Patent Application No. 2010-125379 filed on May 31, 2010, the entire content of which is hereby incorporated by reference.

BACKGROUND OF THE INVENTION

1. Field of the Invention

The present invention relates to a sample analyzer and a reagent information writing method. The present invention particularly relates to a sample analyzer in which reagent containers, to each of which an information storage medium is attached, are mounted and to a reagent information writing method for writing information into the information storage medium.

2. Description of the Related Art

Conventionally, there is known a sample analyzer in which reagent containers, to each of which an information storage medium is attached, are mounted.

For example, Japanese Patent Publication No. 2008/203007 discloses an automatic analyzer including: a reagent cooling box in which reagent containers, to each of which a reagent information tag having reagent information stored therein is attached, are set; a reagent dispensing mechanism for aspirating a reagent from each reagent container; and an antenna for writing information into the reagent information tag. The automatic analyzer is configured such that a position at which each reagent container is located when information is written into the reagent information tag of the reagent container is the same as a position at which the reagent is aspirated from the reagent container. Each time reagent dispensing from a reagent container is performed, a remaining reagent amount written in the reagent information tag of the reagent container is updated.

However, since the automatic analyzer disclosed in Japanese Patent Publication No. 2008/203007 is configured such that the position at which each reagent container is located when information is written into the reagent information tag of the reagent container is the same as the position at which the reagent is aspirated from the reagent container, it is necessary to dispose the reagent dispensing mechanism and the antenna within a limited area. This limits freedom in designing the automatic analyzer.

SUMMARY OF THE INVENTION

The scope of the present invention is defined solely by the appended claims, and is not affected to any degree by the statements within this summary.

A first aspect of the present invention is a sample analyzer for analyzing a sample by using a reagent contained in a reagent container, the sample analyzer comprising: a reagent container holder configured to hold a reagent container to which an information storage medium is attached; an actuator configured to actuate the reagent container holder to move the reagent container held by the reagent container holder to a first position and a second position different from the first position; a reagent aspirator configured to aspirate a reagent from the reagent container when the reagent container is located at the first position; an information communication section configured to write reagent amount information regarding an amount of the reagent in the reagent container, into the information storage medium attached to the reagent container when the reagent container is located at the second position; and a controller configured to control at least the actuator and the information communication section.

A second aspect of the present invention is a reagent information writing method executed by a sample analyzer which analyzes a sample by using a reagent contained in a reagent container, the reagent information writing method comprising steps of: moving a reagent container to a first position; aspirating a reagent from the reagent container when the reagent container is located at the first position; moving the reagent container to a second position different from the first position after the reagent has been aspirated from the reagent container; and writing reagent amount information regarding an amount of the reagent in the reagent container, into an information storage medium attached to the reagent container when the reagent container is located at the second position.

BRIEF DESCRIPTION OF THE DRAWINGS

FIG. 5 is a perspective view showing a reagent setting part of the immune analyzer according to the embodiment of the present invention;

DETAILED DESCRIPTION OF THE PREFERRED EMBODIMENTS

Hereinafter, an embodiment of the present invention will be described with reference to the drawings.

First, a configuration of an immune analyzer 1 according to the embodiment of the present invention will be described with reference to FIG. 1 to FIG. 12.

The immune analyzer 1 according to the embodiment of the present invention is used for performing, in relation to an infectious disease (e.g., hepatitis B or hepatitis C), tests on a sample (e.g., a blood sample) for various items such as proteins, tumor markers, and thyroid hormones.

The immune analyzer 1 performs quantitative measurement or qualitative measurement on an antigen or antibody contained in a sample (such as a blood sample) to be measured. The immune analyzer 1 is configured such that in the case of performing quantitative measurement on an antigen contained in a sample (blood sample), a capture antibody (R1 reagent) bound to the antigen contained in the sample is bound to magnetic particles (R2 reagent), and the antigen, the capture antibody, and the magnetic particles, which have been bound, are attracted to a magnet (not shown) of a primary BF (Bound Free) separator 11. In this manner, the R1 reagent containing the capture antibody that is unreacted (i.e., free) is removed. Then, in the immune analyzer 1, the antigen bound to the magnetic particles is bound to a labeled antibody (R3 reagent). Thereafter, the magnetic particles, the antigen, and the labeled antibody, which have been bound, are attracted to a magnet (not shown) of a secondary BF separator 12. In this manner, the R3 reagent containing the labeled antibody that is unreacted (i.e., free) is removed. Further, a dispersion liquid (R4 reagent) and a luminescent substrate (R5 reagent) which emits light in a reaction process with the labeled antibody are added. Thereafter, the amount of light generated by the reaction of the luminescent substrate with the labeled antibody is measured. Through this process, the antigen contained in the sample, which is bound to the labeled antibody, is quantitatively measured. It should be noted that the immune analyzer 1 is configured to perform analysis on a sample for a plurality of different analysis items.

Figure 1:
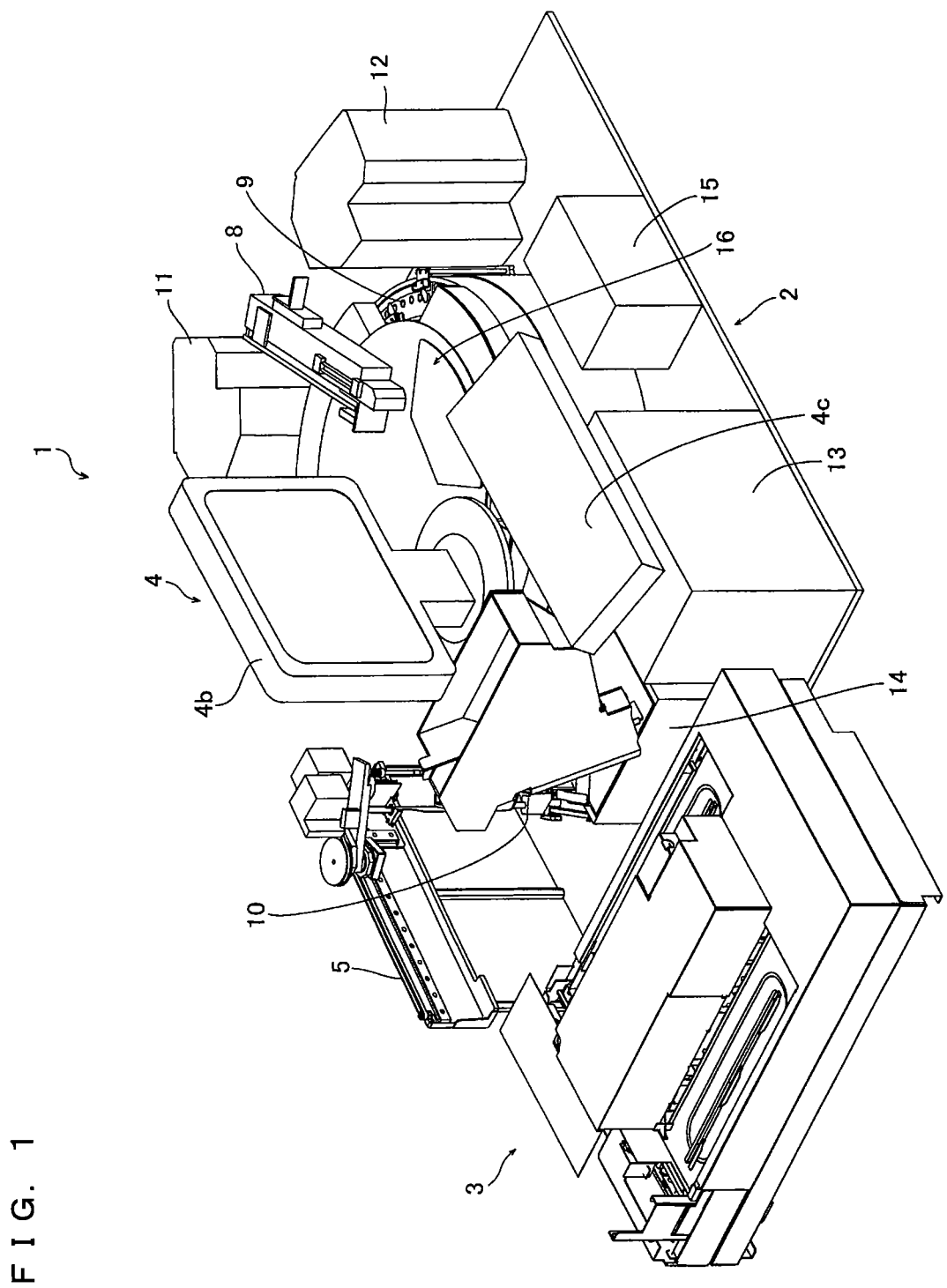
FIG. 1 is a perspective view showing an overall structure of an immune analyzer according to an embodiment of the present invention.
Figure 2:
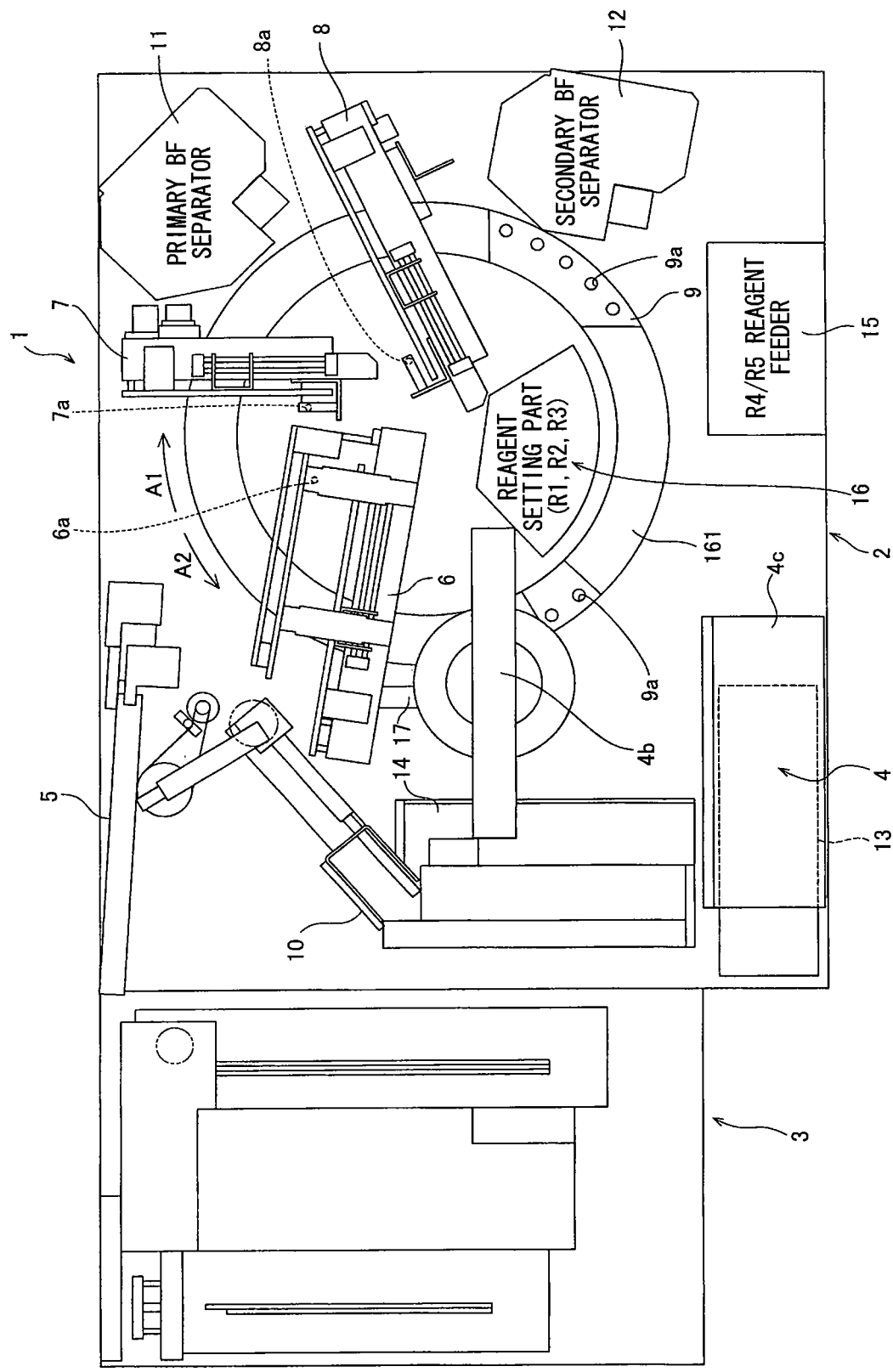
FIG. 2 is a plan view showing an overall structure of the immune analyzer according to the embodiment of the present invention.

As shown in FIG. 1 and FIG. 2, the immune analyzer 1 includes a measurement mechanism unit 2, a sample transporting unit (sampler) 3 disposed adjacent to the measurement mechanism unit 2, and a control apparatus 4 (which is a personal computer) electrically connected to the measurement mechanism unit 2.

The sample transporting unit 3 is configured to transport a rack that accommodates multiple test tubes (not shown) containing samples. Further, the sample transporting unit 3 is configured to transport a test tube containing a sample to a sample aspirating position at which a sample dispensing arm 5 aspirates the sample.

Figure 3:
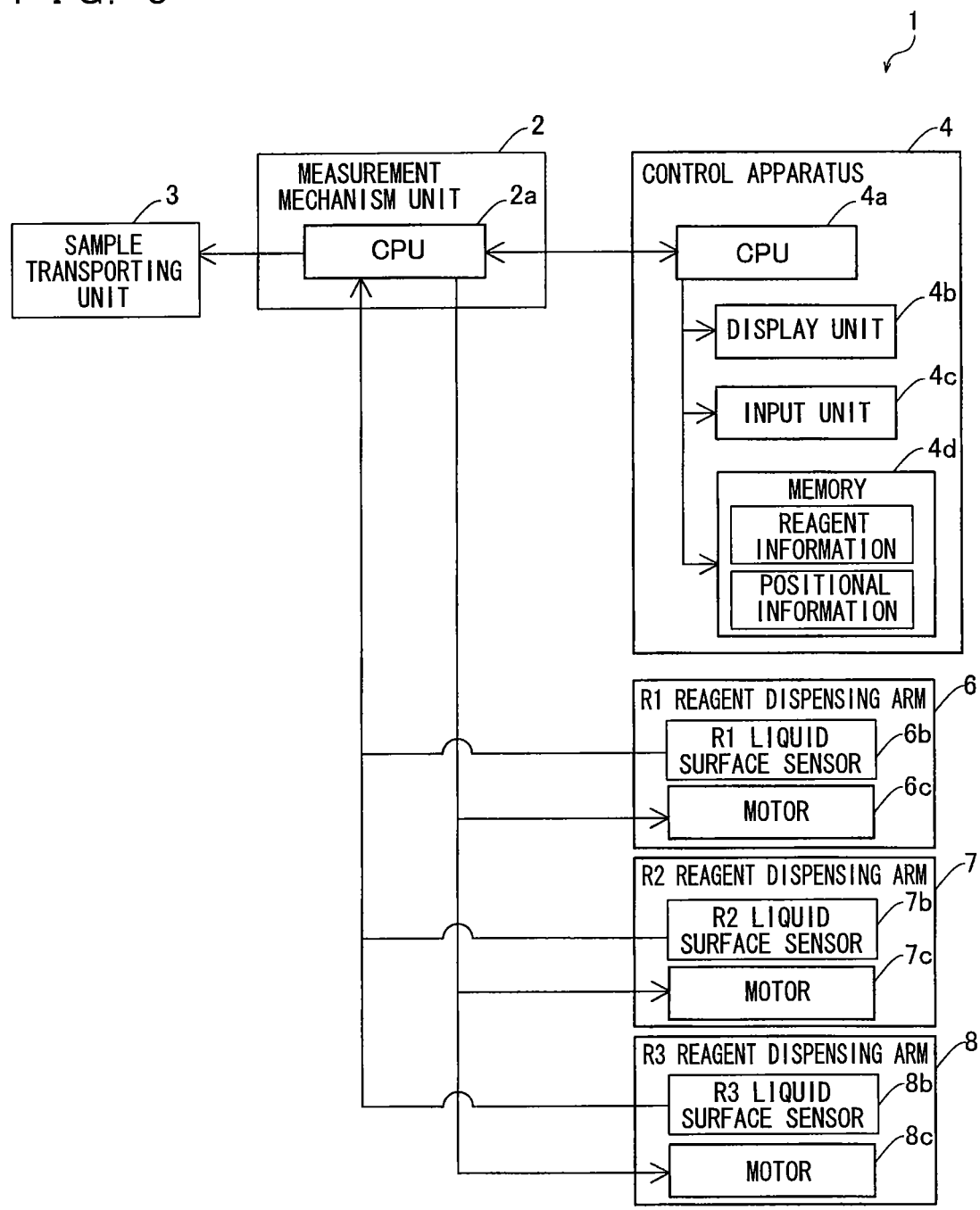
FIG. 3 is a block diagram illustrating a configuration of the immune analyzer according to the embodiment of the present invention.

As shown in FIG. 3, the control apparatus 4 includes a CPU 4a, a display unit 4b, an input unit 4c, and a memory 4d. The CPU 4a causes, based on an analysis instruction that a user has inputted by using the input unit 4c, the measurement mechanism unit 2 (i.e., a CPU 2a which will be described below) to perform measurement. The CPU 4a has functions of analyzing measurement results obtained from the measurement mechanism unit 2 and displaying analysis results on the display unit 4b. The memory 4d includes an HDD (hard disk drive) which stores reagent information and positional information about R1 reagent containers 100, R2 reagent containers 110, and R3 reagent containers 120, which will be described below. The reagent information and positional information are stored for each reagent container, separately. The memory 4d will be described below in detail.

As shown in FIG. 2, the measurement mechanism unit 2 includes the sample dispensing arm 5, an R1 reagent dispensing arm 6, an R2 reagent dispensing arm 7, an R3 reagent dispensing arm 8, a reaction part 9, a cuvette feeder 10, the primary BF separator 11, the secondary BF separator 12, a pipette tip feeder 13, a detector 14, an R4/R5 reagent feeder 15, a reagent setting part 16, and an RFID (Radio Frequency Identification) module 17.

Figure 4:
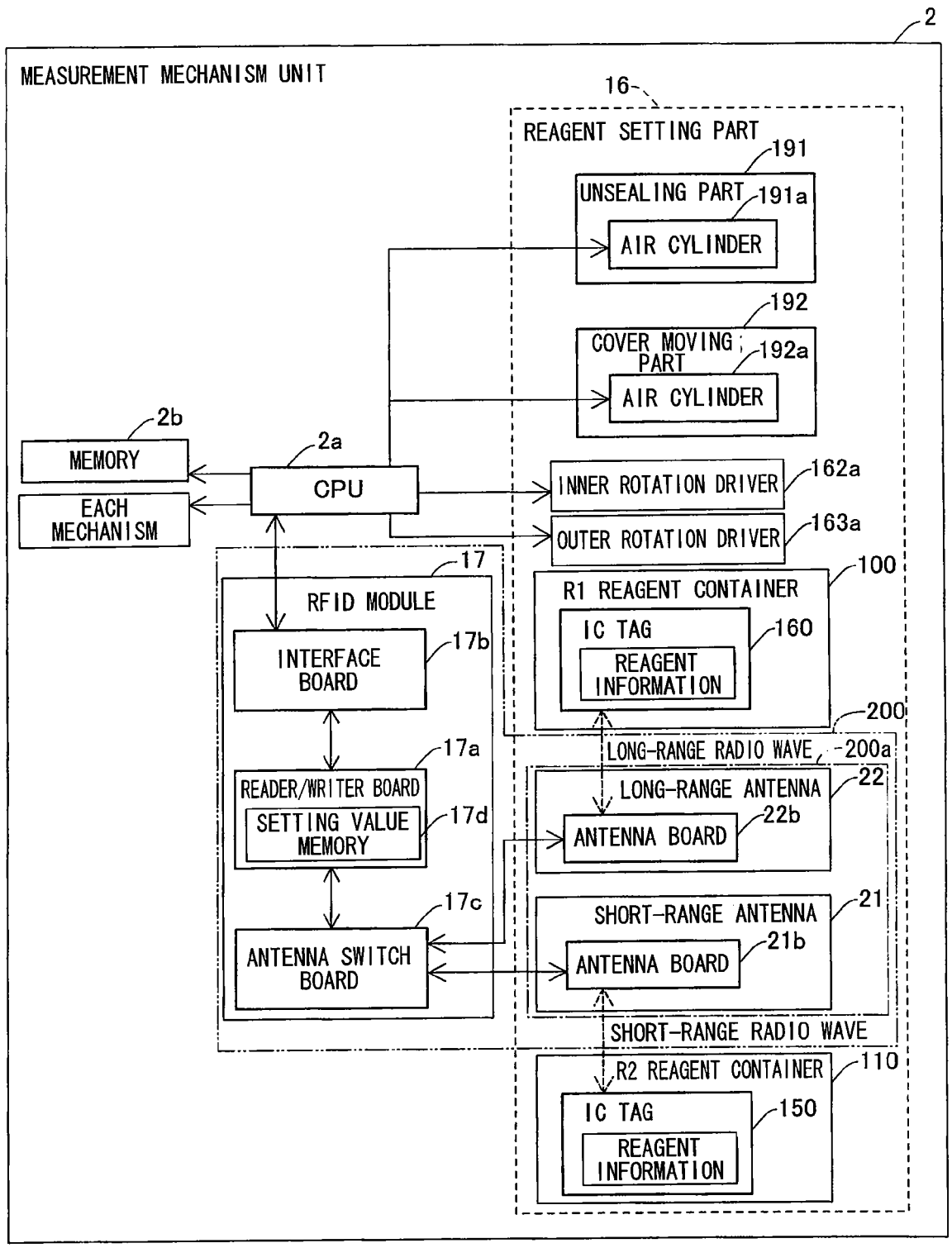
FIG. 4 is a block diagram illustrating a configuration of a measurement mechanism unit according to the embodiment of the present invention.

As shown in FIG. 4, mechanisms in the measurement mechanism unit 2 (i.e., dispensing arms, the reaction part 9, etc) are controlled by the CPU 2a of the measurement mechanism unit 2. The sample transporting unit 3 (see FIG. 3) is also configured to be controlled by the CPU 2a. The measurement mechanism unit 2 includes a memory 2b. The memory 2b stores a control program for causing the CPU 2a to control operations of each mechanism of the measurement mechanism unit 2.

As shown in FIG. 2, the cuvette feeder 10 is configured to accommodate multiple cuvettes (not shown) and has a function of sequentially feeding cuvettes one by one to a sample discharging position at which the sample dispensing arm 5 performs a sample discharging operation.

The R1 reagent dispensing arm 6 is configured to aspirate, at an R1 reagent aspirating position P1a (see FIG. 5) by means of a pipette 6a, the R1 reagent from an R1 reagent container 100 (described below) that is set at the reagent setting part 16, and to dispense (i.e., discharge) the aspirated R1 reagent into a cuvette that is placed at a sample discharging position. Further, the R1 reagent dispensing arm 6 has a function of moving, to the reaction part 9, a cuvette that has been placed at the sample discharging position by a catcher which is not shown.

As shown in FIG. 3, the R1 reagent dispensing arm 6 includes: an R1 liquid surface sensor 6b connected to the pipette 6a (see FIG. 2); and a motor 6c for moving the pipette 6a in the vertical direction to insert the pipette 6a into an R1 reagent container 100. The R1 liquid surface sensor 6b is connected to the CPU 2a, and is configured such that at the time of aspirating the R1 reagent from an R1 reagent container 100, the R1 liquid surface sensor 6b detects the liquid surface of the R1 reagent based on a change in electrostatic capacitance, which change is caused by a contact between the liquid surface of the R1 reagent and the pipette 6a, and outputs a detection result to the CPU 2a. The CPU 2a is configured to monitor the amount of movement of the pipette 6a in the vertical direction by monitoring the rotational amount of the motor 6c.

As shown in FIG. 2, the pipette tip feeder 13 has a function of transporting multiple pipette tips (not shown) that have been fed into the pipette tip feeder 13 to a tip attaching position one by one, at which position a pipette tip is attached to the sample dispensing arm 5. At the tip attaching position, a pipette tip is attached to the end of the pipette of the sample dispensing arm 5.

The sample dispensing arm 5 has functions of aspirating, after the pipette tip is attached to the pipette at the tip attaching position, a sample from a test tube that has been transported to the sample aspirating position by the sample transporting unit 3, and dispensing (i.e., discharging) at the sample discharging position the sample into a cuvette into which the R1 reagent dispensing arm 6 has dispensed the R1 reagent.

The R2 reagent dispensing arm 7 has a function of aspirating, at an R2 reagent aspirating position P2a (see FIG. 5) by means of a pipette 7a, the R2 reagent from an R2 reagent container 110 (described below) that is set at the reagent setting part 16. The R2 reagent dispensing arm 7 is configured to dispense (i.e., discharge) the aspirated R2 reagent into the cuvette that contains the R1 reagent and the sample.

As shown in FIG. 3, the R2 reagent dispensing arm 7 includes: an R2 liquid surface sensor 7b connected to the pipette 7a (see FIG. 2); and a motor 7c for moving the pipette 7a in the vertical direction to insert the pipette 7a into an R2 reagent container 110. The R2 liquid surface sensor 7b is configured such that at the time of aspirating the R2 reagent from an R2 reagent container 110, the R2 liquid surface sensor 7b detects the liquid surface of the R2 reagent based on a change in electrostatic capacitance, which change is caused by a contact between the liquid surface of the R2 reagent and the pipette 7a, and outputs a detection result to the CPU 2a. The CPU 2a is configured to monitor the amount of movement of the pipette 7a in the vertical direction by monitoring the rotational amount of the motor 7c.

As shown in FIG. 2, the reaction part 9 is formed in a substantially annular shape so as to surround the reagent setting part 16 which has a substantially round shape when seen in plan view. The reaction part 9 is configured to rotate in the clockwise direction, which realizes a function of moving cuvettes that are held by cuvette holders 9a to respective positions at which various processes (e.g., reagent dispensing) are performed.

The primary BF separator 11 is configured to separate, after a cuvette that contains a sample, the R1 reagent, and the R2 reagent is moved by a catcher (not shown) from the reaction part 9 to the primary BF separator 11, the R1 reagent that is unreacted (i.e., an unnecessary component) from the magnetic particles in the sample contained in the cuvette (i.e., B/F separation).

The R3 reagent dispensing arm 8 has a function of aspirating, at an R3 reagent aspirating position P3a (see FIG. 5) by means of a pipette 8a, the R3 reagent from an R3 reagent container 120 (described below) that is set at the reagent setting part 16. The R3 reagent dispensing arm 8 is configured to dispense (discharge), when a cuvette that contains a sample for which the primary BF separator 11 has performed the B/F separation is moved from the primary BF separator 11 to the reaction part 9, the aspirated R3 reagent into the cuvette.

As shown in FIG. 3, the R3 reagent dispensing arm 8 includes: an R3 liquid surface sensor 8b connected to the pipette 8a (see FIG. 2); and a motor 8c for moving the pipette 8a in the vertical direction to insert the pipette 8a into an R3 reagent container 120. The R3 liquid surface sensor 8b is configured such that at the time of aspirating the R3 reagent from an R3 reagent container 120, the R3 liquid surface sensor 8b detects the liquid surface of the R3 reagent based on a change in electrostatic capacitance, which change is caused by a contact between the liquid surface of the R3 reagent and the pipette 8a, and outputs a detection result to the CPU 2a. The CPU 2a is configured to monitor the amount of movement of the pipette 8a in the vertical direction by monitoring the rotational amount of the motor 8c.

As shown in FIG. 2, the secondary BF separator 12 is configured to separate, after the cuvette that contains the R3 reagent and the sample for which the primary BF separator 11 has performed the B/F separation is moved by a catcher (not shown) from the reaction part 9 to the secondary BF separator 12, the R3 reagent that is unreacted (i.e., an unnecessary component) from the magnetic particles in the sample contained in the cuvette.

The R4/R5 reagent feeder 15 is configured to dispense, by means of a tube which is not shown, the R4 reagent and the R5 reagent sequentially into the cuvette that contains the sample for which the secondary BF separator 12 has performed the B/F separation.

The detector 14 obtains, by means of a photo multiplier tube, light that is generated in a reaction process between the luminescent substrate and the labeled antibody that is bound to the antigen in the sample on which the above-described predetermined processes have been performed, thereby measuring the amount of the antigen contained in the sample.

Figure 6:
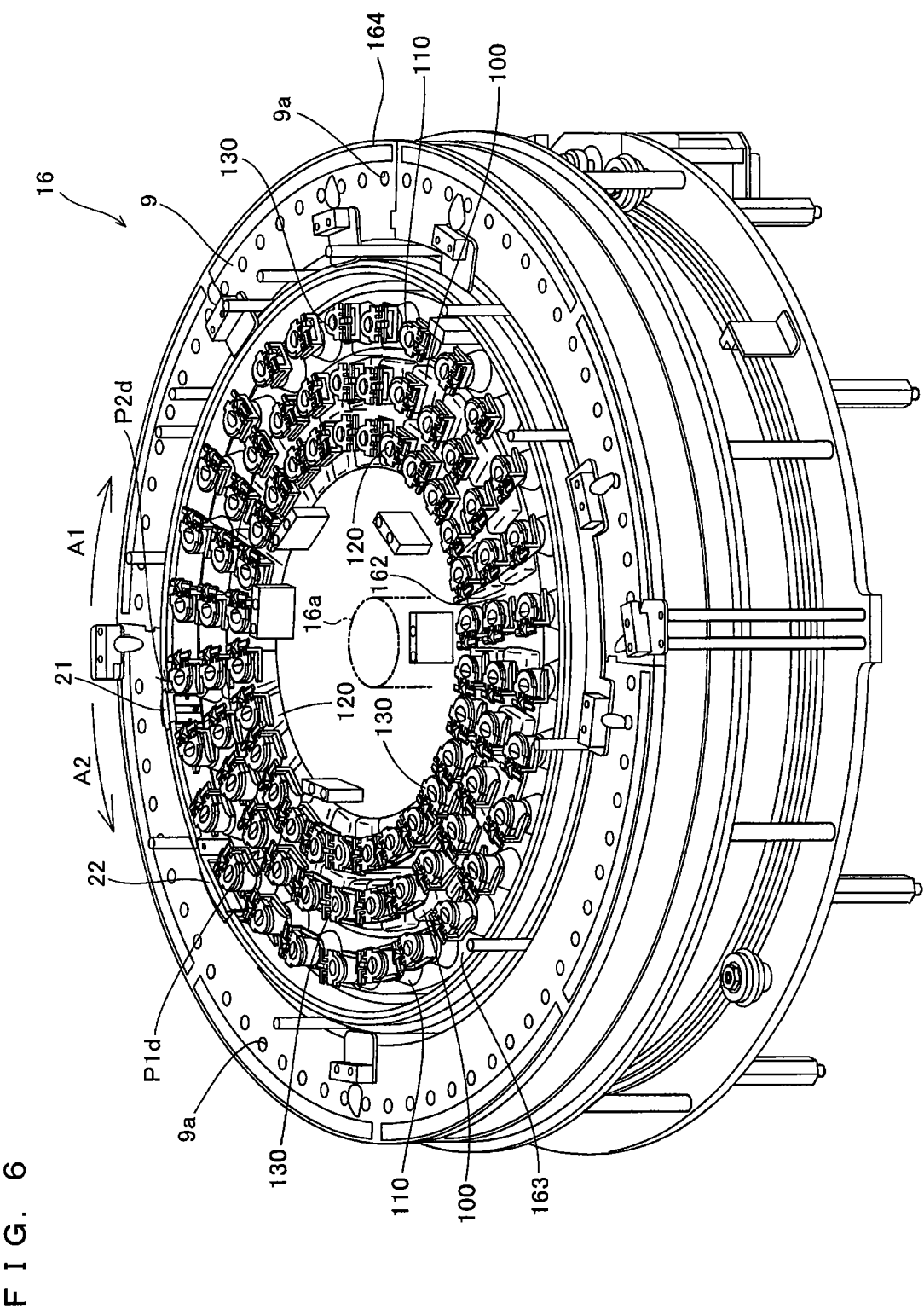
FIG. 6 is a perspective view showing the inside of the reagent setting part of the immune analyzer according to the embodiment of the present invention.

As shown in FIG. 6, the reagent setting part 16 is provided for the purpose of setting thereon a plurality of R1 reagent containers 100 each containing the R1 reagent containing the capture antibody, a plurality of R2 reagent containers 110 each containing the R2 reagent containing the magnetic particles, and a plurality of R3 reagent containers 120 each containing the R3 reagent containing the labeled antibody. The same number of R1 reagent containers 100, R2 reagent containers 110, and R3 reagent containers 120 are set on the reagent setting part 16. The immune analyzer 1 is configured to perform measurement for such measurement items as "HBsAg", "HBeAg", "HBsAb", "HCV", and "HIV" in relation to infectious diseases, and perform measurement for such measurement items as "TSH", "FT3", and "FT4" in relation to hormones. The R1 reagent containers 100, the R2 reagent containers 110, and the R3 reagent containers 120 each contain a reagent that is used for any of the above measurement items, such as a reagent for HBsAg measurement or a reagent for HCV measurement.

The reagent setting part 16 includes: a round-shaped cover 161 as shown in FIG. 2 and FIG. 5; an inner table 162 and an outer table 163 shown in FIG. 6; and a casing 164 which accommodates the inner table 162 and the outer table 163. The cover 161 includes an R1 reagent open/close mechanism 18, an R2 reagent open/close mechanism 19, and an R3 reagent open/close mechanism 20, which are shown in FIG. 5.

As shown in FIG. 2 and FIG. 5, the cover 161 is disposed in a manner to cover both the reagent setting part 16 and the reaction part 9. The round-shaped cover 161 includes an opening 161a, an opening 161b, and an opening 161c which are provided at the R1 reagent aspirating position P1a, the R2 reagent aspirating position P2a, and the R3 reagent aspirating position P3a, respectively. Dispensing operations by the pipettes are performed through these openings 161a, 161b, and 161c.

As shown in FIG. 6, the inner table 162 is configured to hold a plurality of R1 reagent containers 100 and a plurality of R3 reagent containers 120. When seen in plan view, the inner table 162 is formed in an annular shape and has a hollow center. The R1 reagent containers 100 are arranged on the inner table 162 in an annular manner so as to surround the R3 reagent containers 120 which are also arranged on the inner table 162 in an annular manner. The R1 reagent containers 100 are disposed so as to be adjacent, in the radial direction, to the R3 reagent containers 120. The inner table 162 is configured to horizontally rotate in the clockwise direction (arrow A1 direction) and in the counterclockwise direction (arrow A2 direction) with respect to a rotational axis 16a.

Figure 7:
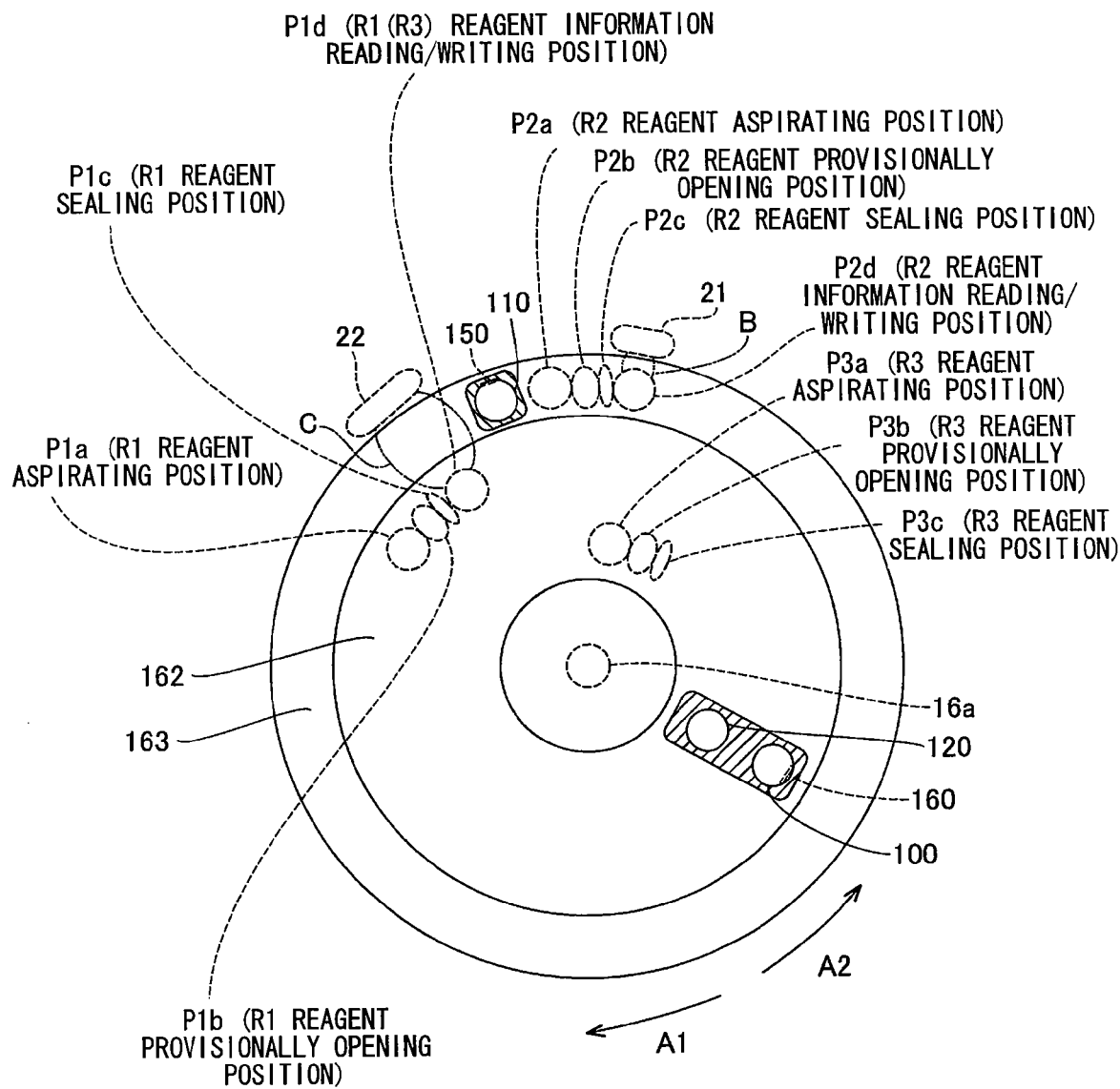
FIG. 7 is a schematic diagram showing the reagent setting part of the immune analyzer according to the embodiment of the present invention.

Specifically, the inner table 162 is configured to rotate with respect to the rotational axis 16a by means of an inner rotation driver 162a (see FIG. 4) which is controlled by the CPU 2a. When the inner table 162 rotates, the R1 reagent containers 100 and the R3 reagent containers 120 rotate in the same direction by the same angle. Accordingly, the inner table 162 is configured to move an R1 reagent container 100 containing the R1 reagent to the R1 reagent aspirating position P1a, an R1 reagent provisionally opening position P1b, an R1 reagent sealing position P1c, and an R1 (R3) reagent information reading/writing position P1d, which are shown in FIG. 7. Also, the inner table 162 is configured to move an R3 reagent container 120 containing the R3 reagent to the R3 reagent aspirating position P3a, an R3 reagent provisionally opening position P3b, and an R3 reagent sealing position P3c.

At the R1 reagent aspirating position P1a, the R1 reagent dispensing arm 6 (see FIG. 2) aspirates the R1 reagent from an R1 reagent container 100. At the R1 reagent provisionally opening position P1b, the R1 reagent open/close mechanism 18 releases the sealing of a below-described cover 130 (see FIG. 6) to the R1 reagent container 100 and thereby the cover 130 is opened by a predetermined amount. At the R1 reagent sealing position P1c, the R1 reagent container 100 is fully sealed, with the cover 130, by the R1 reagent open/close mechanism 18. At the R1 (R3) reagent information reading/writing position P1d, a long-range antenna 22, which will be described below, reads and writes reagent information from and into an IC tag 160 (described below) attached to the R1 reagent container 100.

In the present embodiment, as shown in FIG. 7, the R1 reagent aspirating position P1a and the R1 (R3) reagent information reading/writing position P1d are different positions, and the R1 reagent provisionally opening position P1b and the R1 reagent sealing position P1c are located between the R1 reagent aspirating position P1a and the R1 (R3) reagent information reading/writing position P1d. Specifically, the R1 reagent aspirating position P1a, the R1 reagent provisionally opening position P1b, the R1 reagent sealing position P1c, and the R1 (R3) reagent information reading/writing position P1d are located on the same arc of which the center is the rotational axis 16a. To be more specific, as shown in FIG. 7, these positions (P1a to P1d) are arranged clockwise (in the arrow A1 direction) in the following order: R1 reagent aspirating position P1a, R1 reagent provisionally opening position P1b, R1 reagent sealing position P1c, and R1 (R3) reagent information reading/writing position P1d.

At the R3 reagent aspirating position P3a, the R3 reagent dispensing arm 8 (see FIG. 2) aspirates the R3 reagent from an R3 reagent container 120. At the R3 reagent provisionally opening position P3b, the R3 reagent open/close mechanism 20 releases the sealing of the below-described cover 130 (see FIG. 6) to the R3 reagent container 120 and thereby the cover 130 is opened by a predetermined amount. At the R3 reagent sealing position P3c, the R3 reagent container 120 is fully sealed, with the cover 130, by the R3 reagent open/close mechanism 20. As shown in FIG. 7, the R3 reagent aspirating position P3a, the R3 reagent provisionally opening position P3b, and the R3 reagent sealing position P3c are located on the same arc of which the center is the rotational axis 16a. These positions are arranged clockwise (in the arrow A1 direction) in the following order: R3 reagent aspirating position P3a, R3 reagent provisionally opening position P3b, and R3 reagent sealing position P3c.

As shown in FIG. 6, the outer table 163 is configured to hold a plurality of R2 reagent containers 110, and is formed in an annular shape and has a hollow center so as to surround the inner table 162. The outer table 163 is configured to hold the same number of R2 reagent containers 110 as the number of R1 reagent containers 100 and the number of R3 reagent containers 120 that are holdable by the inner table 162. The R2 reagent containers 110 are arranged on the outer table 163 in an annular manner so as to surround the R1 reagent containers 100 which are also arranged in an annular manner. The outer table 163 is configured to horizontally rotate in the clockwise direction (the arrow A1 direction) and the counterclockwise direction (the arrow A2 direction) with respect to the rotational axis 16a.

To be specific, the outer table 163 is configured to rotate with respect to the rotational axis 16a by means of an outer rotation driver 163a (see FIG. 4) which is controlled by the CPU 2a. The outer table 163 is rotatable independently of the inner table 162. This allows the outer table 163 to rotate the R2 reagent containers 110 in either direction at any speed without being affected by the speed and direction of the rotation of the R1 reagent containers 100 and the R3 reagent containers 120. Accordingly, the outer table 163 is configured to move an R2 reagent container 110 containing the R2 reagent to the R2 reagent aspirating position P2a, an R2 reagent provisionally opening position P2b, an R2 reagent sealing position P2c, and an R2 reagent information reading/writing position P2d, as shown in FIG. 7.

At the R2 reagent aspirating position P2a, the R2 reagent dispensing arm 7 (see FIG. 2) aspirates the R2 reagent from an R2 reagent container 110. At the R2 reagent provisionally opening position P2b, the R2 reagent open/close mechanism 19 releases the sealing of the below-described cover 130 (see FIG. 6) to the R2 reagent container 110 and thereby the cover 130 is opened by a predetermined amount. At the R2 reagent sealing position P2c, the R2 reagent container 110 is fully sealed, with the cover 130, by the R2 reagent open/close mechanism 19. At the R2 reagent information reading/writing position P2d, a short-range antenna 21, which will be described below, reads and writes reagent information from and into an IC tag 150 (described below) attached to the R2 reagent container 110.

In the present embodiment, as shown in FIG. 7, the R2 reagent aspirating position P2a and the R2 reagent information reading/writing position P2d are different positions, and the R2 reagent provisionally opening position P2b and the R2 reagent sealing position P2c are located between the R2 reagent aspirating position P2a and the R2 reagent information reading/writing position P2d. Specifically, the R2 reagent aspirating position P2a, the R2 reagent provisionally opening position P2b, the R2 reagent sealing position P2c, and the R2 reagent information reading/writing position P2d are located on the same arc of which the center is the rotational axis 16a. To be more specific, as shown in FIG. 7, these positions (P2a to P2d) are arranged clockwise (in the arrow A1 direction) in the following order: R2 reagent aspirating position P2a, R2 reagent provisionally opening position P2b, R2 reagent sealing position P2c, and R2 reagent information reading/writing position P2d.

The R1 reagent open/close mechanism 18, the R2 reagent open/close mechanism 19, and the R3 reagent open/close mechanism 20 have the same configuration. Hereinafter, the configuration of the R2 reagent open/close mechanism 19 will be described.

Figure 8:
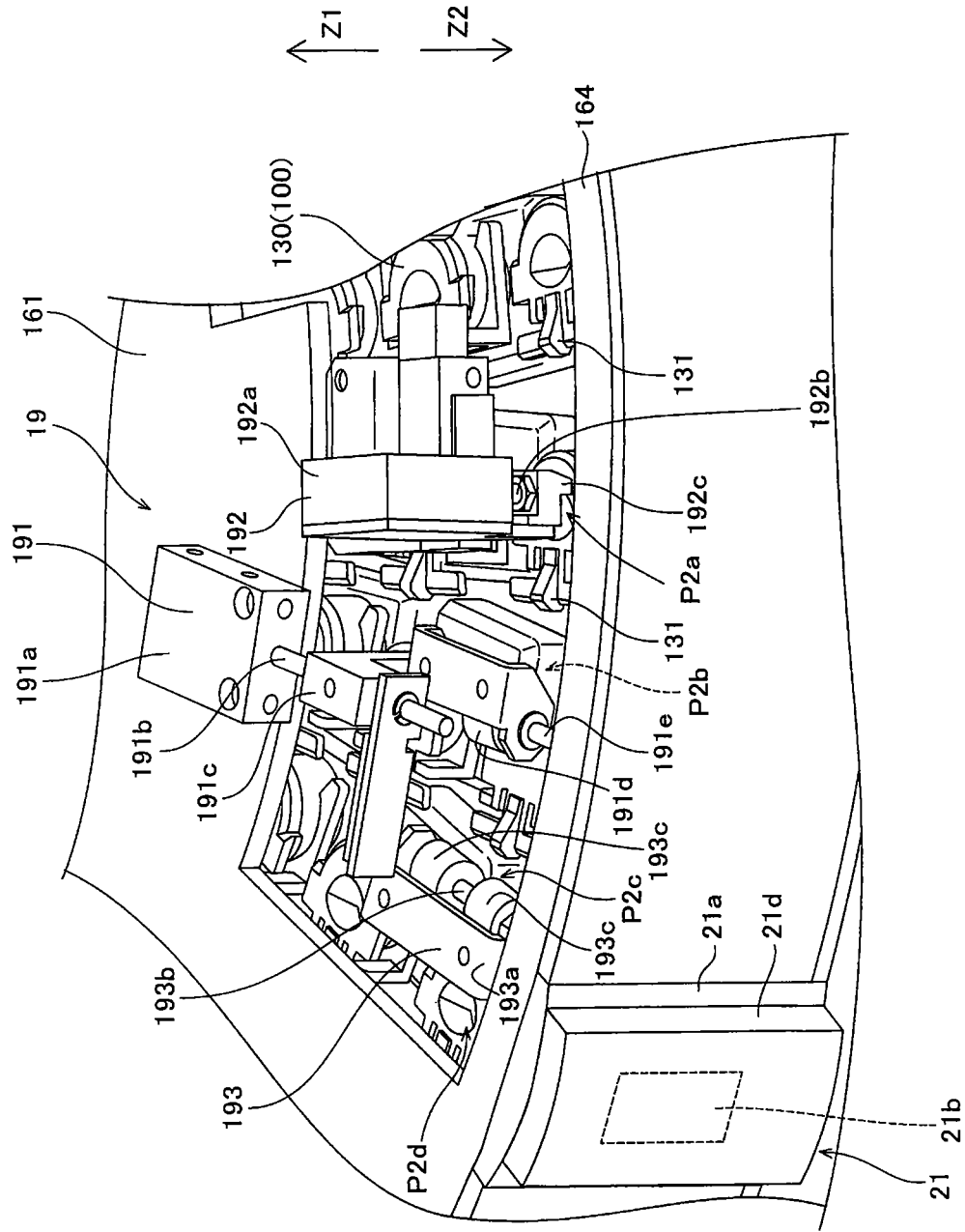
FIG. 8 is an enlarged perspective view showing a part of the reagent setting part of the immune analyzer according to the embodiment of the present invention.

The R2 reagent open/close mechanism 19 includes an unsealing part 191, a cover moving part 192, and an opening sealing part 193, as shown in FIG. 8.

The unsealing part 191 includes an air cylinder 191a set on the cover 161, a shaft 191b, a fitting 191c, an unsealing roller 191d, and a roller shaft 191e for pivotally supporting the unsealing roller 191d. The shaft 191b and the roller shaft 191e are connected by the fitting 191c. The unsealing roller 191d is disposed at such a height as to allow the unsealing roller 191d and a protruding portion 131 (see FIG. 11) of the below-described cover 130 of an R2 reagent container 110 held by the outer table 163 to come into contact with each other. The unsealing part 191 is configured such that when the air cylinder 191a is driven, the unsealing roller 191d moves horizontally and linearly in the radial direction of the cover 161 (i.e., an arrow X1 direction or an arrow X2 direction shown in FIG. 14) via the shaft 191b, the fitting 191c, and the roller shaft 191e. This allows the unsealing roller 191d to move to a position where the unsealing roller 191d and the protruding portion 131 of the cover 130 come into contact with each other or to a position where the unsealing roller 191d and the protruding portion 131 do not come into contact with each other. The sealing by the cover 130 is released in the following manner: move the unsealing roller 191d to such a position as to allow the unsealing roller 191d and the protruding portion 131 of the cover 130 to come into contact with each other, and then rotate the outer table 163 to cause the protruding portion 131 of the cover 130 of the R2 reagent container 110 and the unsealing roller 191d to come into contact with each other.

The cover moving part 192 includes an air cylinder 192a disposed on the cover 161, a shaft 192b, and a pressing member 192c. The cover moving part 192 is configured such that when the air cylinder 192a is driven, the pressing member 192c linearly moves in the vertical direction (i.e., the arrow Z1 direction or the arrow Z2 direction) via the shaft 192b. Accordingly, the protruding portion 131 of the cover 130 can be pressed downward (in the arrow Z2 direction) by the pressing member 192c when the projecting portion 131 of the cover 130 is located at a predetermined position.

The opening sealing part 193 includes a fitting 193a, a roller shaft 193b, and two rollers 193c. The fitting 193a is attached to the back face of the cover 161 (see FIG. 5). The two rollers 193c are configured to rotate with respect to the roller shaft 193b which is the rotational center. The two rollers 193c have functions of returning the state of an R2 reagent container 110 that is being moved owing to the rotation of the outer table 163, to a sealed state by being contacted by the cover 130 of the R2 reagent container 110. The two rollers 193c are spaced apart with a predetermined distance so as not to be contacted by the protruding portion 131 of the cover 130 of the R2 reagent container 110. Accordingly, when seen in plan view, the protruding portion 131 of each R2 reagent container 110 moved by the rotation of the outer table 163 passes through the space between the two rollers 193c.

As shown in FIG. 5 and FIG. 6, the casing 164 of the reagent setting part 16 is provided with the short-range antenna 21 and the long-range antenna 22. The short-range antenna 21 and the long-range antenna 22 are both attached to the side of the casing 164 of the reagent setting part 16. It should be noted that as shown in FIG. 6, the short-range antenna 21 and the long-range antenna 22 are both provided at the outer periphery of the outer table 163.

The R2 reagent information reading/writing position P2d is provided at a position where a line connecting an antenna board 21b (described below) of the short-range antenna 21 and the rotational axis 16a intersects the outer table 163. Similarly, the R1 (R3) reagent information reading/writing position P1d is provided at a position where a line connecting an antenna board 22b (described below) of the long-range antenna 22 and the rotational axis 16a intersects the inner table 162.

Figure 9:
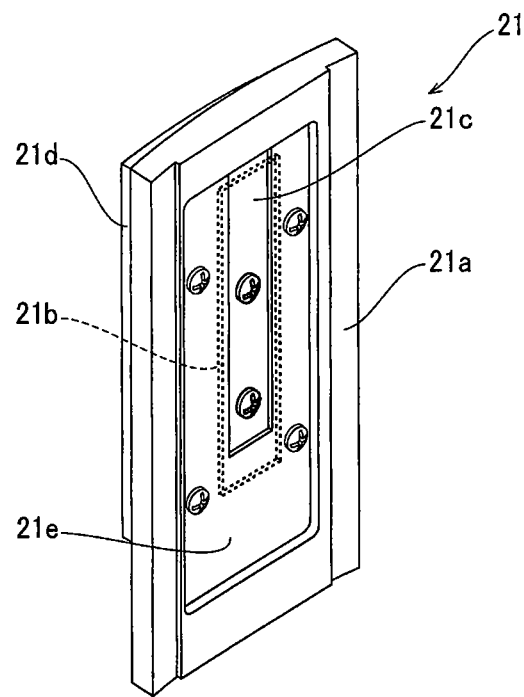
FIG. 9 is a perspective view showing a short-range antenna of the reagent setting part according to the embodiment of the present invention.

As shown in FIG. 9, the short-range antenna 21 includes: a locking portion 21a for locking the short-range antenna 21 to the casing 164 (see FIG. 6); the antenna board 21b in the shape of a flat plate; a board fitting portion 21c within which the antenna board 21b is fixed; a cover 21d for covering the antenna board 21b from the outside (i.e., from a side opposite to the rotational axis 16a side shown in FIG. 6); and a metal plate 21e for limiting radio waves from the antenna board 21b.

Figure 10:
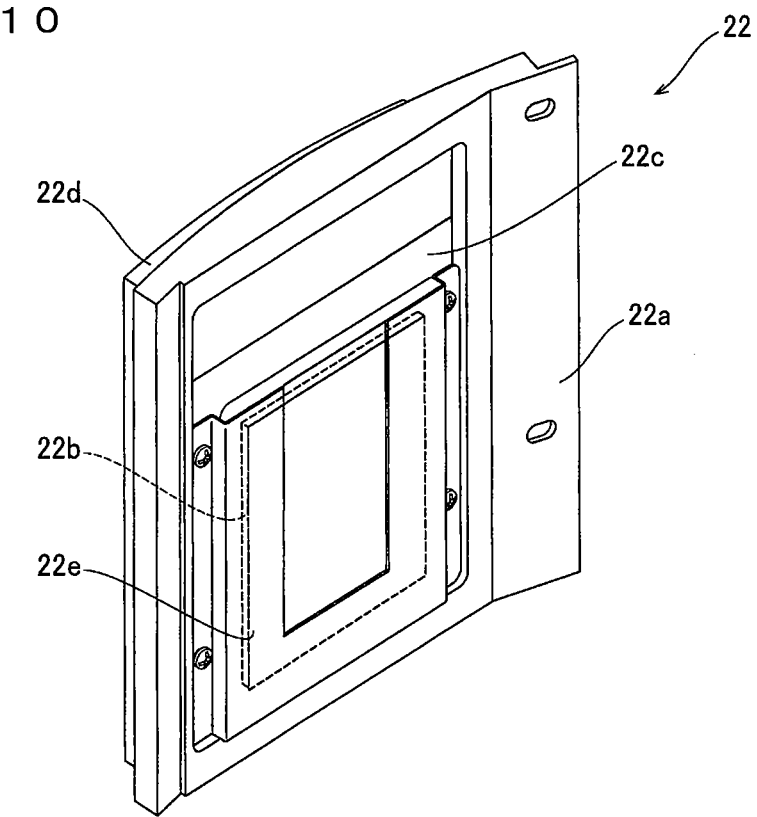
FIG. 10 is a perspective view showing a long-range antenna of the reagent setting part according to the embodiment of the present invention.

As shown in FIG. 10, the long-range antenna 22 includes: a locking portion 22a for locking the long-range antenna 22 to the casing 164; the antenna board 22b in the shape of a flat plate; a board fitting portion 22c within which the antenna board 22b is fixed; a cover 22d for covering the antenna board 22b from the outside; and a metal plate 22e for limiting radio waves from the antenna board 22b.

As shown in FIG. 7, the antenna board 21b of the short-range antenna 21 is configured to transmit short-range radio waves for reading and short-range radio waves for writing, the range of both of which is a range B, thereby reading and writing reagent information from and into the IC tag 150 (described below) attached to an R2 reagent container 110. Similarly, the antenna board 22b of the long-range antenna 22 is configured to transmit long-range radio waves for reading and long-range radio waves for writing, the range of both of which is a range C wider than the range B, thereby reading and writing reagent information from and into the IC tag 160 (described blow) attached to an R1 reagent container 100. The short-range antenna 21 is configured such that the reading range and the writing range of the short-range antenna 21 are smaller than the reading range and the writing range of the long-range antenna 22. As shown in FIG. 4, the antenna board 21 b and the antenna board 22b are connected to an antenna switch board 17c (described below) of the RFID module 17.

Figure 11:
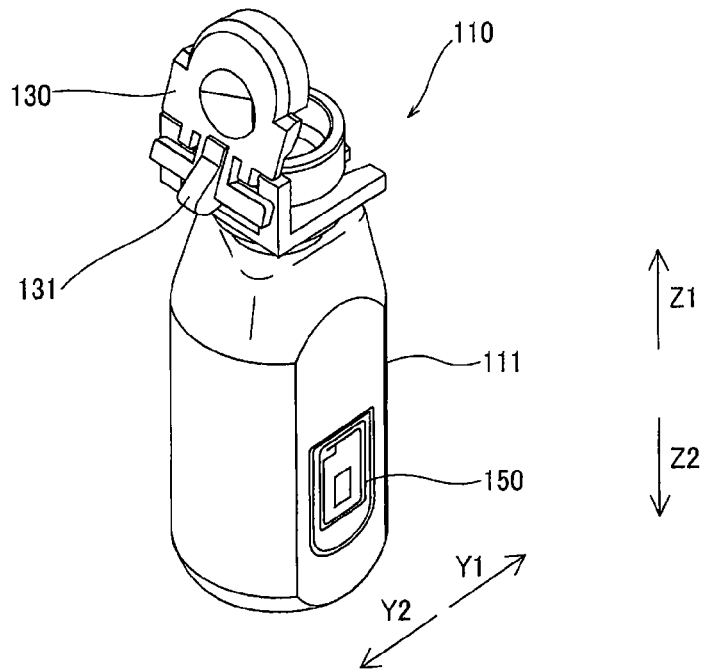
FIG. 11 is a perspective view showing an R2 reagent container according to the embodiment of the present invention.

The R1 reagent container 100, R2 reagent container 110, and R3 reagent container 120 have the same configuration. As shown in FIG. 11, the R2 reagent container 110 includes a container body 111 and a cover 130 for sealing the container body 111. The cover 130 is supported in a pivotable manner. The cover 130 has the protruding portion 131 which is configured to come into contact with the unsealing roller 191d.

As shown in FIG. 11, the IC tag 150 is attached to one of the sides of the R2 reagent container 110. As shown in FIG. 7, the IC tag 150 is attached to the R2 reagent container 110 such that when the R2 reagent container 110 is placed on the outer table 163, the IC tag 150 faces outward from the reagent setting part 16 (i.e., faces not the rotational axis 16a but the opposite side). The IC tag 150 stores reagent information about the R2 reagent in the R2 reagent container 110.

As shown in FIG. 7, the IC tag 160 is attached to one of the sides of the R1 reagent container 100. The IC tag 160 is attached to the R1 reagent container 100 such that when the R1 reagent container 100 is placed on the inner table 162, the IC tag 160 faces outward from the reagent setting part 16 (i.e., faces not the rotational axis 16a but the opposite side). The IC tag 160 stores reagent information about the R1 reagent in the R1 reagent container 100 and reagent information about the R3 reagent in the R3 reagent container 120 that is adjacent, in the radial direction, to the R1 reagent container 100. No IC tag is attached to the R3 reagent container 120.

Figure 12:
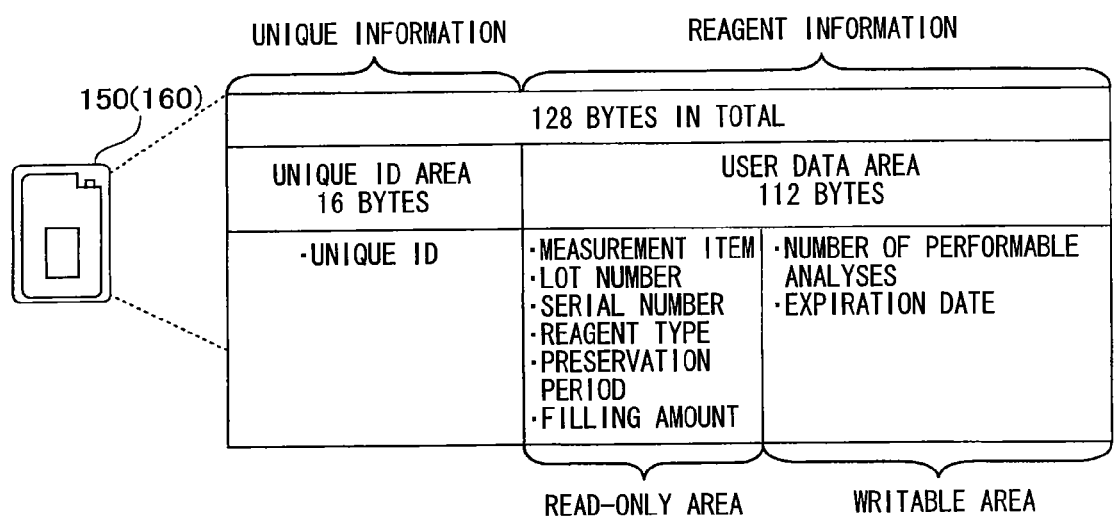
FIG. 12 is a conceptual diagram showing unique information and reagent information which are stored in an IC tag according to the embodiment of the present invention.

As shown in FIG. 12, each of the IC tag 150 and the IC tag 160 is configured to store information of 128 bytes. Of the storage capacity of 128 bytes, 16 bytes are allocated for a unique ID area which indicates unique information, and 112 bytes are allocated for a user data area which indicates reagent information. The unique ID area stores a unique ID for identifying the IC tag 150 (or 160), and is a read-only storage area. The user data area allows the user to freely write information therein. The user data area includes an area from which data stored therein is readable but into which data is not writable (i.e., a read-only area), and an area from which data stored therein is readable and into which data is writable (i.e., a writable area).

The unique ID is used when the CPU 2a encrypts the reagent information. Accordingly, even if the reagent information is copied to another IC tag, the copied reagent information cannot be decrypted since the unique ID of the other IC tag is not an ID associated with the reagent information. This reduces the possibility that the reagent information is improperly associated with the reagent of a wrong reagent container.

The read-only area stores information about R1 and R3 reagent containers 100 and 120, or information about an R2 reagent container 110. The information about each reagent container contains, for example, a measurement item, a lot number, a serial number, a reagent type (type identification information), a preservation period, and a filling amount. In the writable area, the number of performable analyses and an expiration date are written. It should be noted that the IC tag 160 stores information about an R3 reagent container 120 in addition to information about an R1 reagent container 100.

In the IC tag (both 150 and 160), the measurement item indicates a measurement that uses the reagent contained in the reagent container to which the IC tag is attached. The reagent type indicates whether the reagent container to which the IC tag is attached is an R1 reagent container 100 or an R2 reagent container 110. The preservation period indicates until when the reagent in the reagent container can be preserved. The filling amount indicates the total number of times the analysis can be performed by using the reagent. The number of performable analyses indicates how many more times the analysis can be performed by using the reagent. The IC tag stores in advance the number of performable analyses at the initial point. Each time reagent aspiration is performed, 1 is subtracted from the number of performable analyses at the initial point, and the resultant value is written into the IC tag. The expiration date indicates until when the reagent can be used. The expiration date is set when the reagent starts being used.

Referring to FIG. 7, the IC tag 150 of the R2 reagent container 110 is configured such that reading and writing of the reagent information from and into the IC tag 150 are performed when the IC tag 150 is located at a position at which the IC tag 150 faces the short-range antenna 21 (i.e., a facing position). The IC tag 150 is configured such that when the IC tag 150 is located at the facing position, the IC tag 150 transmits response radio waves containing the reagent information stored in the IC tag 150, in response to the short-range (range B) radio waves for reading which are transmitted from the short-range antenna 21. Also, the IC tag 150 is configured such that when the IC tag 150 is located at the facing position, the reagent information stored in the IC tag 150 is overwritten with new reagent information contained in the short-range (range B) radio waves for writing which are transmitted from the short-range antenna 21.

The IC tag 160 of the R1 reagent container 100 is configured such that reading and writing of the reagent information from and into the IC tag 160 are performed when the IC tag 160 is located at a position at which the IC tag 160 faces the long-range antenna 22 (i.e., a facing position). The IC tag 160 is configured such that when the IC tag 160 is located at the facing position, the IC tag 160 transmits response radio waves containing the reagent information stored in the IC tag 160, in response to the long-range (range C) radio waves for reading which are transmitted from the long-range antenna 22. Also, the IC tag 160 is configured such that when the IC tag 160 is located at the facing position, the reagent information stored in the IC tag 160 is overwritten with new reagent information contained in the long-range (range C) radio waves for writing which are transmitted from the long-range antenna 22.

Referring to FIG. 3, the reagent information about a plurality of R1 reagent containers 100, a plurality of R2 reagent containers 110, and a plurality of R3 reagent containers 120 is stored not only in the IC tags 150 and 160 but also in the memory 4d of the control apparatus 4. The reagent information is stored in the memory 4d for each reagent container separately. The memory 4d stores the following information as positional information: the initial position of each of the R1 reagent containers 100, R2 reagent containers 110, and R3 reagent containers 120; and the rotation angle of the inner table 162 with respect to its initial position and the rotational angle of the outer table 163 with respect to its initial position. Accordingly, the memory 4d stores the positional information about the R1 reagent containers 100, R2 reagent containers 110, and R3 reagent containers 120 in association with the reagent information about the R1 reagent containers 100, R2 reagent containers 110, and R3 reagent containers 120.

As shown in FIG. 2, the RFID module 17 is provided at the outside of the reagent setting part 16. As shown in FIG. 4, the RFID module 17 includes a reader/writer board 17a, an interface board 17b which acts as an intermediary between the reader/writer board 17a and the CPU 2a, and the antenna switch board 17c.

The reader/writer board 17a is configured to cause, in accordance with instructions from the CPU 2a, the short-range antenna 21 (or the long-range antenna 22) to transmit short-range radio waves for reading (or long-range radio waves for reading) and short-range radio waves for writing (or long-range radio waves for writing) at the frequency band of approximately 13.56 MHz. Moreover, the reader/writer board 17a is configured to obtain reagent information from response radio waves, which the IC tag 150 (or the IC tag 160) transmits in response to the short-range radio waves for reading (or the long-range radio waves for reading) and which are received by the short-range antenna 21 (or the long-range antenna 22), and to output the obtained reagent information to the CPU 2a.

The reader/writer board 17a includes a setting value memory 17d for storing setting values associated with the antenna board 21b, setting values associated with the antenna board 22b, and setting values of transmitter power output to the antenna boards 21b and 22b. These setting values are set by the CPU 2a. The antenna switch board 17c has functions of receiving, from the reader/writer board 17a, signals that correspond to setting values stored in the setting value memory 17d, and switching, based on the received signals, the use of antenna between the short-range antenna 21 and the long-range antenna 22 for transmitting and receiving radio waves for reading and radio waves for writing.

In the present embodiment, as shown in FIG. 4, a reagent information reader/writer 200 is provided for reading the reagent information stored in the IC tags 150 and 160 by means of the RFID module 17, the short-range antenna 21, and the long-range antenna 22. The short-range antenna 21 and the long-range antenna 22 for transmitting radio waves to the IC tag 150 and the IC tag 160, respectively, collectively act as a radio wave transmitter 200a.

Described next with reference to FIG. 13 to FIG. 21 is an R2 reagent aspirating process operation performed by the immune analyzer 1 (the measurement mechanism unit 2) according to the embodiment of the present invention.

First, at step S1, the CPU 2a determines whether a reagent aspirating instruction to aspirate the reagent from an R2 reagent container 110, which reagent aspirating instruction is based on an analysis instruction given from the user, has been received from the control apparatus 4. If it is determined at step S1 that a reagent aspirating instruction has been received, then at step S2, the CPU 2a determines an R2 reagent container 110 that is a reagent aspirating target. To be specific, among the R2 reagent containers 110, an R2 reagent container 110 that contains the R2 reagent corresponding to an analysis item specified based on the analysis instruction from the user is determined to be a reagent aspirating target. It should be noted that, hereinafter, an R2 reagent container that is currently determined to be a reagent aspirating target is an "R2 reagent container 110a", and an R2 reagent container that is determined to be a reagent aspirating target at the next time is an "R2 reagent container 110b". If it is determined at step S1 that no reagent aspirating instruction has been given, then the determination at step S1 is repeated.

Figure 14:
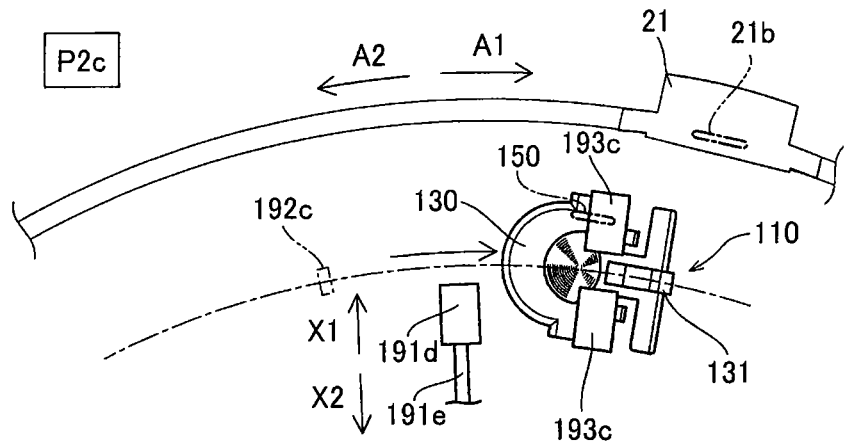
FIG. 14 shows a state where the R2 reagent container is located at a start position, according to the embodiment of the present invention.
Figure 15:
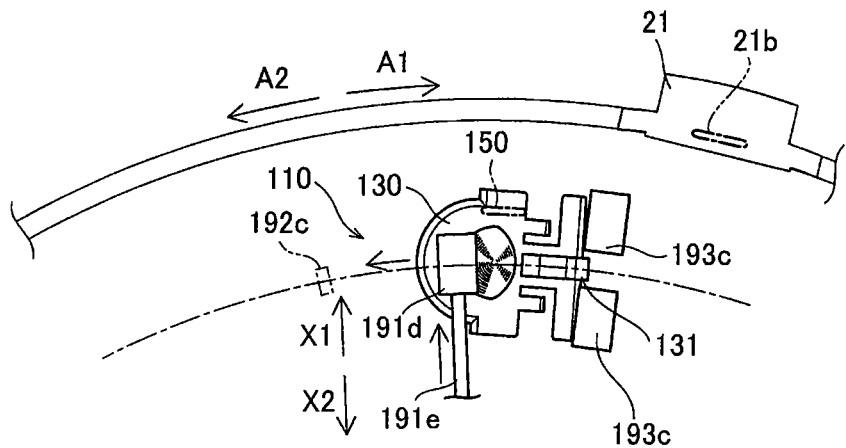
FIG. 15 shows the R2 reagent container moving toward an R2 reagent provisionally opening position P2*b*, according to the embodiment of the present invention.

Next, at step S3, in response to an instruction from the CPU 2a, the outer rotation driver 163a causes the outer table 163 to rotate with respect to the rotational axis 16a in the arrow A1 direction (i.e., clockwise). Accordingly, as shown in FIG. 14, the R2 reagent container 110a, which is a reagent aspirating target, passes by the unsealing roller 191d of the unsealing part 191, and thereafter, arrives at the vicinity of the two rollers 193c of the opening sealing part 193 (i.e., arrives at a start position). Also, at step S3, the air cylinder 191a of the unsealing part 191 is driven, and thereby the unsealing roller 191d is moved to such a position (see FIG. 15) as to allow the unsealing roller 191d and the protruding portion 131 of the R2 reagent container 110a which is a reagent aspirating target to come into contact with each other.

Figure 16:
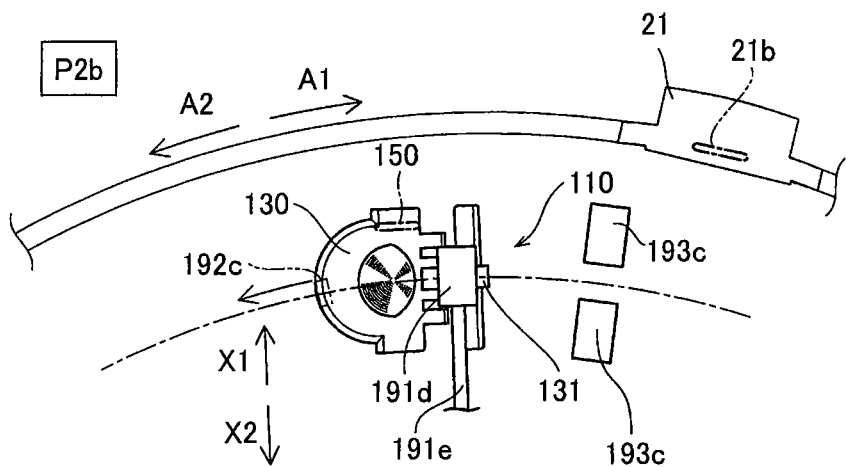
FIG. 16 shows the R2 reagent container moving toward an R2 reagent aspirating position P2*a*, according to the embodiment of the present invention.
Figure 17:
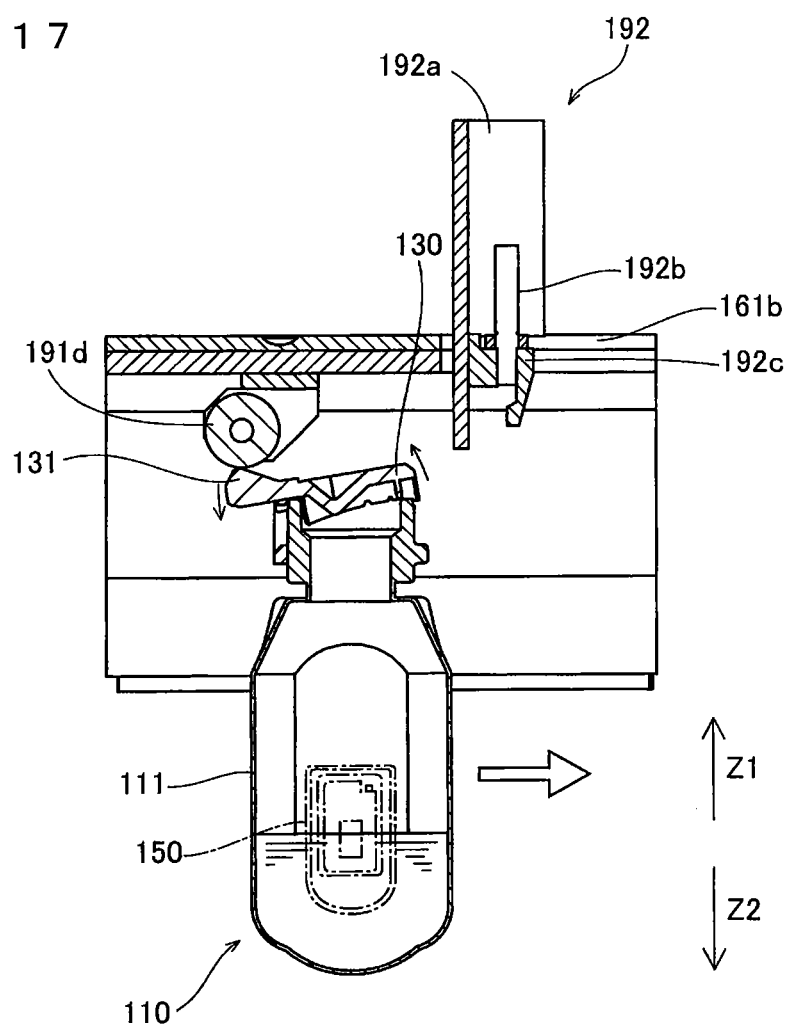
FIG. 17 is a cross-sectional view showing a provisionally opened state in the reagent aspirating process operation, according to the embodiment of the present invention.

Next, at step S4, in response to an instruction from the CPU 2a, the outer rotation driver 163a causes the outer table 163 to rotate with respect to the rotational axis 16a in the arrow A2 direction (i.e., counterclockwise) such that the R2 reagent container 110a moves toward the R2 reagent aspirating position P2a. Accordingly, the R2 reagent container 110a is moved to the R2 reagent provisionally opening position P2b. At this time, as shown in FIG. 16, the unsealing roller 191d comes into contact with the protruding portion 131 of the cover 130. Then, the R2 reagent container 110a continues to move in the counterclockwise direction (the arrow A2 direction). As a result, as shown in FIG. 17, the protruding portion 131 side of the cover 130 is gradually pressed downward by the unsealing roller 191d. Accordingly, the cover 130 is gradually lifted. In this manner, the cover 130 is provisionally opened.

Figure 18:
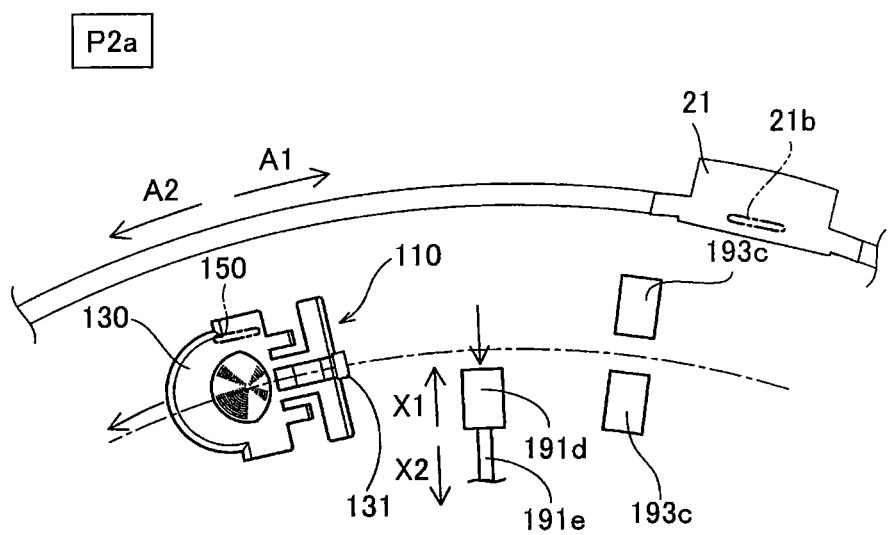
FIG. 18 shows a state where the R2 reagent container is located at an R2 reagent aspirating position P2a, according to the embodiment of the present invention.
Figure 19:
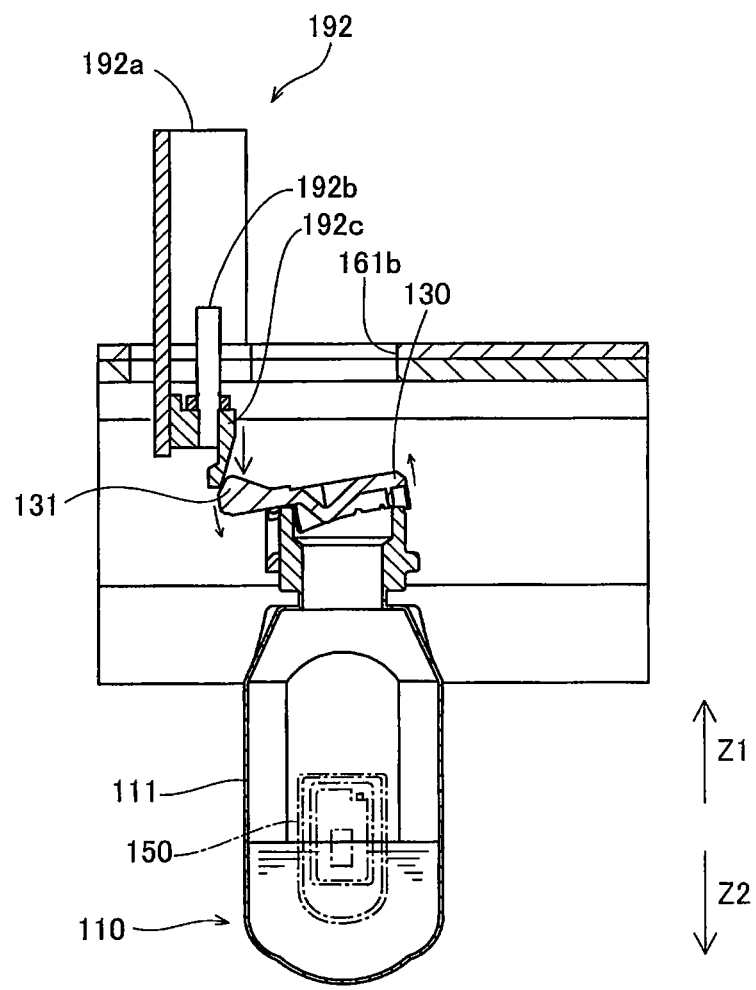
FIG. 19 is a cross-sectional view showing an opened state in the reagent aspirating process operation, according to the embodiment of the present invention.
Figure 20:
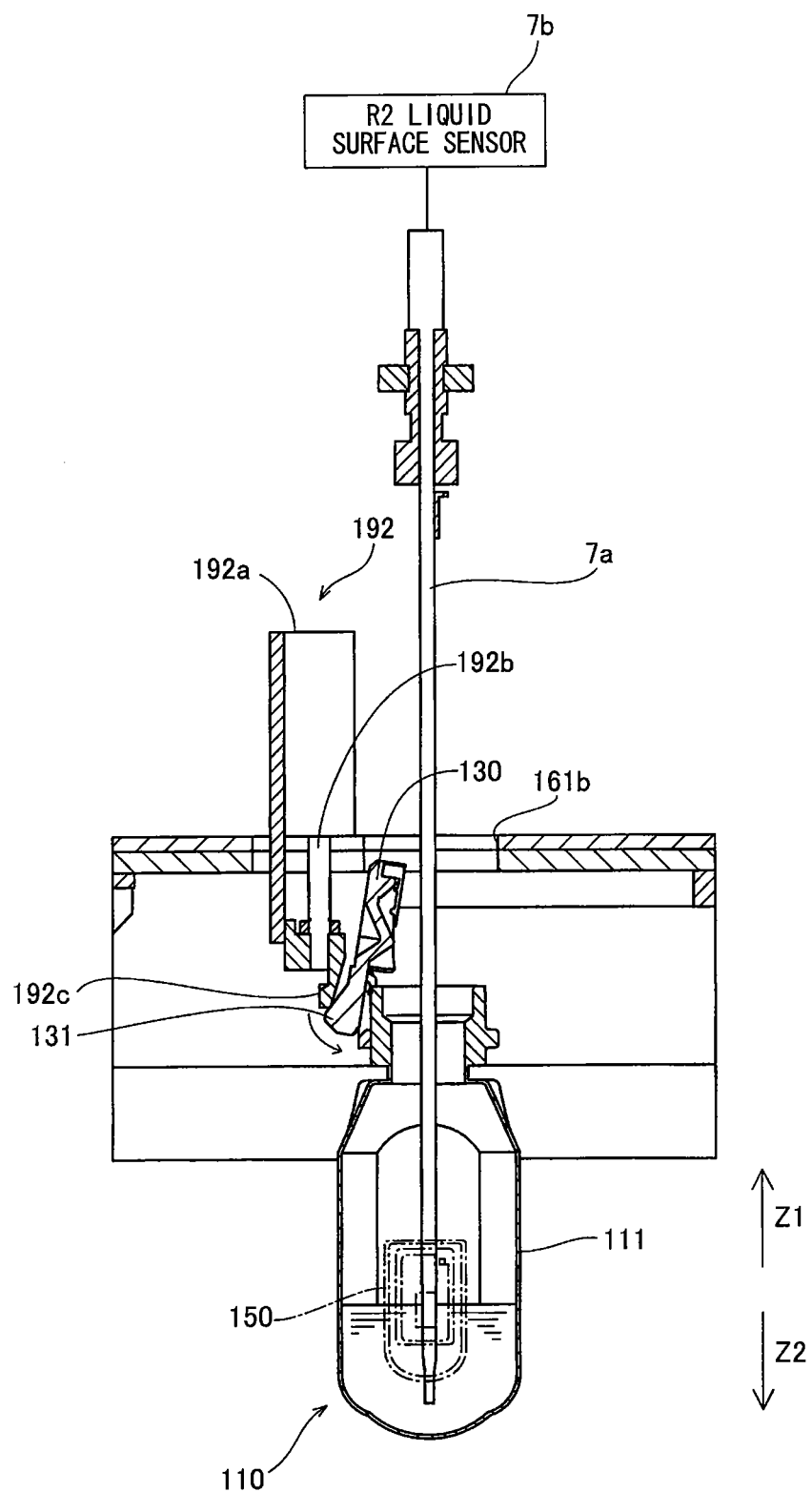
FIG. 20 is a cross-sectional view showing a state where a reagent is aspirated in the reagent aspirating process operation, according to the embodiment of the present invention.

Thereafter, as shown in FIG. 18, the protruding portion 131 of the R2 reagent container 110a arrives at the R2 reagent aspirating position P2a. Then, at step S5, in response to an instruction from the CPU 2a, the air cylinder 191a of the unsealing part 191 is driven, and thereby the unsealing roller 191d returns to its original position at which the unsealing roller 191d and the protruding portion 131 do not come into contact with each other, and also, the air cylinder 192a of the cover moving part 192 is driven, and thereby the pressing member 192c is lowered. As a result, as shown in FIG. 19, the protruding portion 131 is pressed downward by the pressing member 192c, and the opening of the R2 reagent container 110a is fully opened (i.e., opened state). Thereafter, as shown in FIG. 20, the pipette 7a of the R2 reagent dispensing arm 7 is inserted via the opening into the container body 111 of the R2 reagent container 110a.

Subsequently, at step S6, the CPU 2a determines, based on a detection result that is obtained by the R2 liquid surface sensor 7b when the pipette 7a is inserted into the container body 111 of the R2 reagent container 110a, whether a predetermined amount of R2 reagent to be aspirated is present within the R2 reagent container 110a. If it is determined at step S6 that the predetermined amount of R2 reagent is not present within the R2 reagent container 110a, then at step S7, aspiration error information indicating that the R2 reagent cannot be aspirated is transmitted to the control apparatus 4 (see FIG. 3). Then, the R2 reagent aspirating process operation ends.

If it is determined at step S6 that the predetermined amount of R2 reagent is present within the R2 reagent container 110a, then at step S8, the R2 reagent is aspirated by an amount that is necessary for the analysis. After the R2 reagent has been aspirated, the CPU 2a drives the air cylinder 192a at step S9, and thereby the pressing member 192c is lifted, and also, the pipette 7a is lifted. As a result, the opened state is cancelled, and the cover 130 is returned to such a position as to cover the opening of the R2 reagent container 110a.

Figure 21:
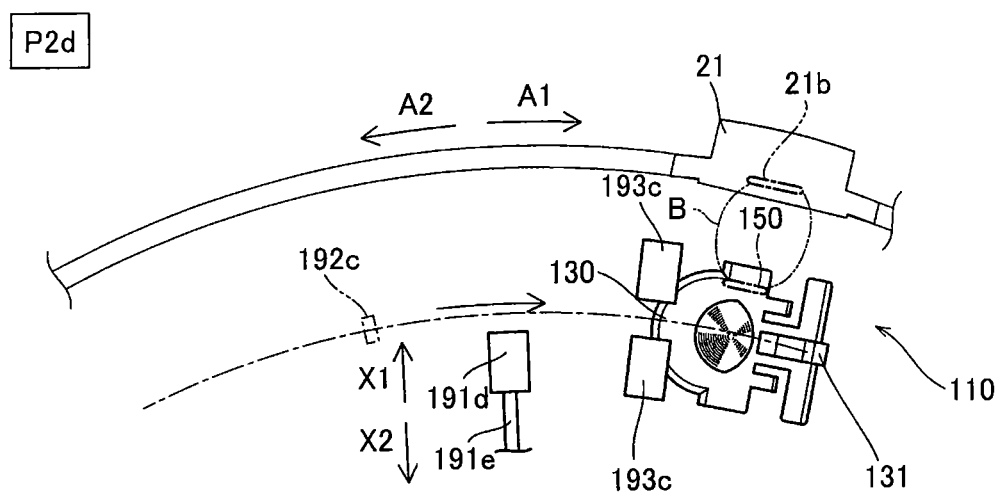
FIG. 21 shows a state where the R2 reagent container is located at an R2 reagent information reading/writing position P2d, according to the embodiment of the present invention.

At step S10, in response to an instruction from the CPU 2a, the outer rotation driver 163a causes the outer table 163 to rotate with respect to the rotational axis 16a in the arrow A1 direction (i.e., clockwise) such that the R2 reagent container 110a moves from the R2 reagent aspirating position P2a toward the R2 reagent information reading/writing position P2d. Accordingly, the R2 reagent container 110a from which the R2 reagent has been aspirated is moved to the R2 reagent sealing position P2c (see FIG. 14). At the R2 reagent sealing position P2c, the cover 130, which is not fully sealing the R2 reagent container 110a, comes into contact with the two rollers 193c located in the advancing direction of the R2 reagent container 110a. Accordingly, the cover 130 is pressed downward, and thereby the R2 reagent container 110a returns to the fully sealed state. Then, as shown in FIG. 21, the R2 reagent container 110a from which the R2 reagent has been aspirated is located at the R2 reagent information reading/writing position P2d.

Thereafter, at step S11, the CPU 2a determines whether the R2 reagent has been properly aspirated by the amount that is necessary for the analysis. At this time, the CPU 2a determines whether the R2 reagent has been properly aspirated by the amount that is necessary for the analysis, based on a liquid surface position detection result which the R2 liquid surface sensor 7b obtains when the R2 liquid surface sensor 7b emerges from the liquid surface of the R2 reagent in the R2 reagent container 110a, and based on the amount of rotation of the motor 8c. If it is determined at step S11 that the R2 reagent has not been properly aspirated by the amount that is necessary for the analysis, then at step S7, aspiration error information indicating that the R2 reagent has not been properly aspirated is transmitted to the control apparatus 4. Thereafter, the R2 reagent aspirating process operation ends.

If it is determined at step S11 that the R2 reagent has been properly aspirated by the amount that is necessary for the analysis, then at step S12, the CPU 2a performs a reagent information reading/writing process operation. The reagent information reading/writing process operation will be described below in detail.

After the reagent information reading/writing process operation has ended, the CPU 2a determines at step S13 whether the next reagent aspirating instruction to aspirate the R2 reagent from an R2 reagent container 110 has been given. If it is determined at step S13 that the next reagent aspirating instruction has been given, the processing returns to step S2 at which the CPU 2a determines the R2 reagent container 110b which is the next reagent aspirating target.

Here, either of the following may be determined to be the R2 reagent container 110b which is the next reagent aspirating target: an R2 reagent container 110 that is different from the R2 reagent container 110a from which the R2 reagent has previously been aspirated; or the R2 reagent container 110 from which the R2 reagent has previously been aspirated. It should be noted that if the analysis item, lot number, expiration date, etc., of the previously aspirated R2 reagent are the same as those of the R2 reagent that is to be aspirated next, then the R2 reagent container 110a which was the previous reagent aspirating target is determined to be the next reagent aspirating target (i.e., determined to be the R2 reagent container 110b).

After step S2, a series of reagent aspirating operation and reagent information reading/writing process operation is performed on the R2 reagent container 110b which is the next reagent aspirating target. Accordingly, the immune analyzer 1 aspirates the reagent from the R2 reagent container 110a which is the first reagent aspirating target and performs reading from and writing into the IC tag 150 attached to the R2 reagent container 110a, and after such a series of operations, the immune analyzer 1 opens the cover 130 of the R2 reagent container 110b which is the second reagent aspirating target and aspirates the reagent from the R2 reagent container 110b. On the other hand, if it is determined at step S13 that the next reagent aspirating instruction has not been given, the R2 reagent aspirating process operation ends.

Figure 13:
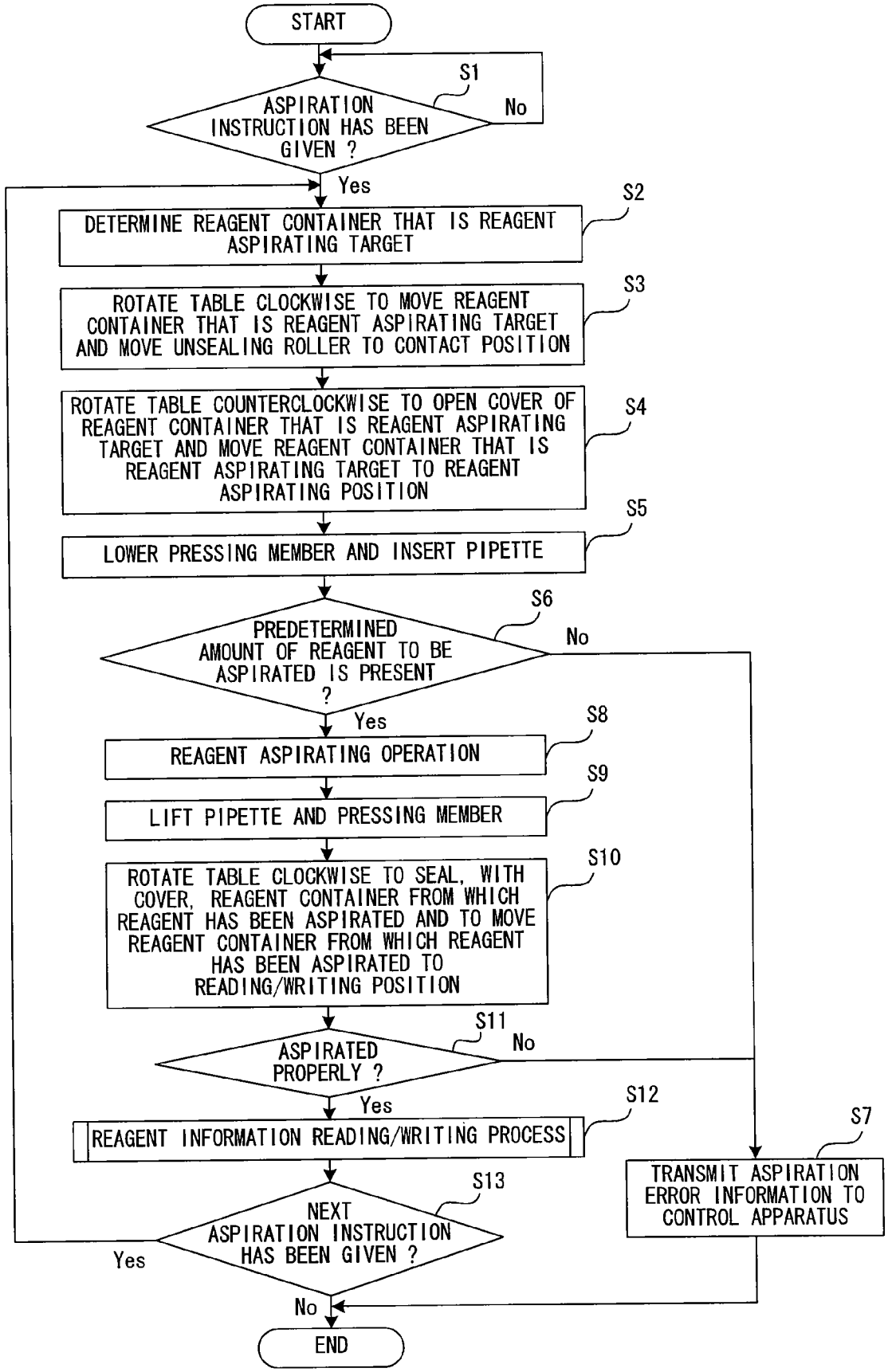
FIG. 13 is a flowchart showing a reagent aspirating process operation performed by the immune analyzer according to the embodiment of the present invention.
Figure 22:
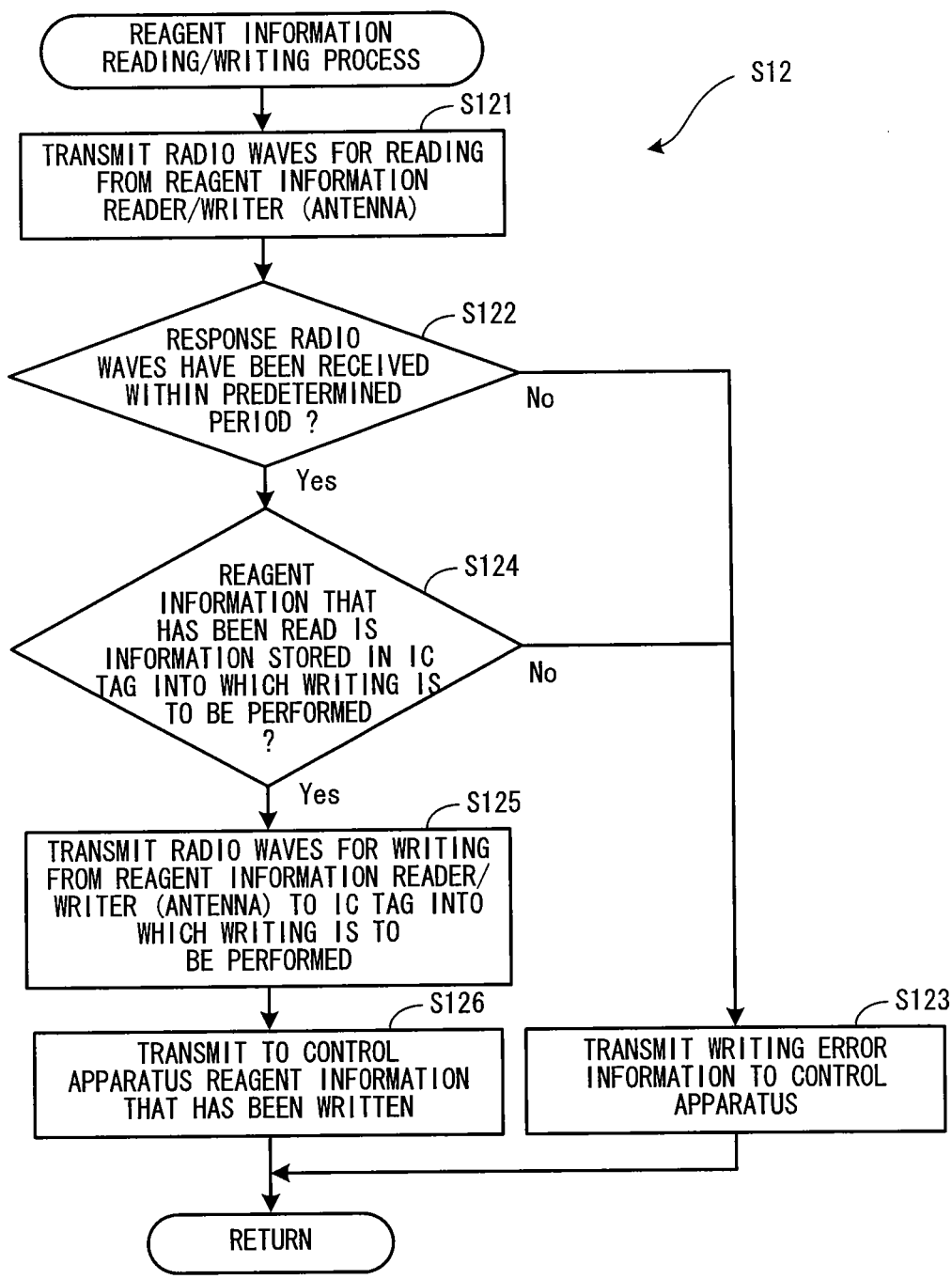
FIG. 22 is a flowchart showing a reagent information reading/writing process operation according to the embodiment of the present invention.

Hereinafter, the reagent information reading/writing process operation which is performed at step S12 of FIG. 13 by the immune analyzer 1 (the measurement mechanism unit 2) according to the embodiment of the present invention will be described in detail with reference to FIG. 21 and FIG. 22.

First, at step S121, the CPU 2a causes the short-range antenna 21 of the reagent information reader/writer 200 to transmit the short-range (range B) radio waves for reading (as shown in FIG. 21) to the IC tag 150 of the R2 reagent container 110 that is located at the R2 reagent information reading/writing position P2d. Thereafter, at step S122, the CPU 2a determines whether the short-range antenna 21 has received response radio waves within a predetermined period. If it is determined at step S122 that the short-range antenna 21 has not received response radio waves within the predetermined period, then at step S 123, the CPU 2a transmits writing error information to the control apparatus 4. Accordingly, the reagent information reading/writing process operation ends and the processing proceeds to step S13 shown in FIG. 13.

If it is determined at step S122 that the short-range antenna 21 has received response radio waves within the predetermined period, then at step S124, the CPU 2a determines whether the response radio waves have been received from the IC tag 150 into which writing is to be performed. At this time, the CPU 2a determines, based on the measurement item, lot number, serial number, and reagent type that are contained in reagent information obtained from the response radio waves, whether the response radio waves have been received from the IC tag 150 into which writing is to be performed. It should be noted that whether the response radio waves have been received from the IC tag 150 into which writing is to be performed may be determined based on a unique ID obtained from the response radio waves. If it is determined that the response radio waves have not been received from the IC tag 150 into which writing is to be performed, the processing proceeds to the above-described step S123.

If it is determined that the response radio waves have been received from the IC tag 150 into which writing is to be performed, then at step S125, short-range radio waves for writing, which contain reagent information including the number of performable analyses, are transmitted from the short-range antenna 21 of the reagent information reader/writer 200 to the IC tag 150 of the R2 reagent container 110 from which the R2 reagent has been aspirated, and the reagent information is written into the IC tag 150. Then, at step S126, after the CPU 2a has transmitted to the control apparatus 4 the same information as the reagent information that has been written into the IC tag 150, the reagent information reading/writing process operation ends and the processing proceeds to step S13 shown in FIG. 13. It should be noted that in the control apparatus 4, the reagent information stored in the memory 4d is updated with the reagent information transmitted from the CPU 2a.

It should be noted that an R1 reagent aspirating process operation and an R3 reagent aspirating process operation are performed in the same manner as that of the R2 reagent aspirating process operation.

As described above, according to the present embodiment, the reagent aspirating positions and the reagent information reading/writing positions are different from each other. Therefore, it is not necessary to position the antennas in relation to the reagent aspirating positions at which reagents are aspirated from reagent containers, or to position the reagent dispensing arms in relation to the reagent information reading/writing positions at which reagent information is written into IC tags. This increases freedom in designing the immune analyzer 1. Moreover, while the writing of reagent amount information into the IC tag of a reagent container from which a reagent has been aspirated is being performed at a reagent information reading/writing position, an operation of aspirating a reagent from a reagent container that is the next reagent aspirating target can be performed at a reagent aspirating position. This improves the processing capacity of the immune analyzer 1.

Further, as described above in the present embodiment, after a series of operations, i.e., reagent aspiration from the R2 reagent container 110a and writing into the IC tag 150 attached to the R2 reagent container 110a, is completed, the cover 130 of the R2 reagent container 110b which is the next reagent aspirating target is opened and the reagent is aspirated from the R2 reagent container 110b. Therefore, as compared to a case where the reagent is aspirated from the R2 reagent container 110b which is the next reagent aspirating target and then reagent information is written into the IC tag 150 of the R2 reagent container 110a which was the reagent aspirating target prior to the R2 reagent container 110b, a change in the amount of R2 reagent present in the R2 reagent container 110a can be more promptly reflected in the information stored in the IC tag 150 attached to the R2 reagent container 110a. Furthermore, since the reagent information is written into the IC tag 150 of the R2 reagent container 110a before the cover 130 of the R2 reagent container 110b which is the next reagent aspirating target is opened, even if an abnormality occurs in the immune analyzer 1 and thereby the immune analyzer 1 stops operating after the cover 130 of the R2 reagent container 110b which is the next reagent aspirating target is opened, a change in the reagent information can be assuredly reflected in the information stored in the IC tag 150 of the R2 reagent container 110a which was the reagent aspirating target prior to the R2 reagent container 110b.

Still further, as described above in the present embodiment, if the analysis item, lot number, expiration date, etc., of the R2 reagent that has been aspirated are the same as those of the R2 reagent that is to be aspirated next, then the R2 reagent container 110a from which the R2 reagent has been aspirated is used as the R2 reagent container 110b which is the next reagent aspirating target. Accordingly, even in a case where the R2 reagent is aspirated from the same R2 reagent container 110 multiple times consecutively, reagent information can be written into the IC tag 150 each time the R2 reagent is aspirated.

Still further, as described above in the present embodiment, each of the IC tags 150 and 160 stores, as reagent information (reagent amount information), the number of performable analyses, which indicates how many more times the analysis can be performed by using the reagent in the corresponding reagent container. Accordingly, the number of performable analyses using the reagent in the reagent container to which the IC tag 150 (or 160) is attached can be readily confirmed.

Still further, as described above in the present embodiment, the CPU 2a determines, based on a detection result that is obtained by the R2 liquid surface sensor 7b when the pipette 7a is inserted into the container body 111 of an R2 reagent container 110, whether a predetermined amount of R2 reagent to be aspirated is present within the R2 reagent container 110. In this manner, whether the predetermined amount of R2 reagent is present within the R2 reagent container 110 can be confirmed when the pipette 7a is inserted into the container body 111 of the R2 reagent container 110. This makes it possible to determine, prior to aspirating the R2 reagent, whether the R2 reagent can be aspirated.

Still further, as described above in the present embodiment, at the reagent aspirating positions, the respective liquid surface sensors each electrically detect a reagent surface position in a reagent container based on a change in electrostatic capacitance at the liquid surface of a reagent in the reagent container, and at the reagent information reading/writing positions, the respective antennas each transmit radio waves for reading and radio waves for writing. According to this configuration, the influence of radio waves from the antennas is kept small at the reagent aspirating positions. This reduces a possibility that any of the liquid surface sensors becomes unable to properly detect a liquid surface position.

Still further, as described above in the present embodiment, in response to an instruction from the CPU 2a, the outer rotation driver 163a causes the outer table 163 to rotate with respect to the rotational axis 16a such that an R2 reagent container 110 from which the R2 reagent has been aspirated is moved from the R2 reagent aspirating position P2a toward the R2 reagent information reading/writing position P2d in the arrow A1 direction (i.e., clockwise). As a result, the R2 reagent container 110 is moved to the R2 reagent sealing position P2c. Then, the cover 130, which is not fully sealing the R2 reagent container 110, comes into contact with the two rollers 193c located in the advancing direction of the R2 reagent container 110. Accordingly, the cover 130 is pressed downward, and thereby the R2 reagent container 110 returns to the fully sealed state. In this manner, the R2 reagent container 110 can be sealed with the cover 130 which is pressed by a force that is generated from the movement of the R2 reagent container 110 from the R2 reagent aspirating position P2a toward the R2 reagent information reading/writing position P2d. Thus, it is not necessary to additionally provide a drive source for sealing the R2 reagent container 110 with the cover 130. Since moving the R2 reagent container 110 to the R2 reagent information reading/writing position P2d and sealing the R2 reagent container 110 with the cover 130 can be performed in parallel, a time required for moving the R2 reagent container 110 to the R2 reagent information reading/writing position P2d and closing the cover 130 can be reduced.

Still further, as described above in the present embodiment, in response to an instruction from the CPU 2a, the outer rotation driver 163a causes the outer table 163 to rotate with respect to the rotational axis 16a such that the R2 reagent container 110 is moved from the R2 reagent information reading/writing position P2d toward the R2 reagent aspirating position P2a in the arrow A2 direction (i.e., counterclockwise). As a result, the cover 130 is provisionally opened at the R2 reagent provisionally opening position P2b. Also, when the outer table 163 is caused to rotate with respect to the rotational axis 16a such that the R2 reagent container 110 is moved from the R2 reagent aspirating position P2a toward the R2 reagent information reading/writing position P2d in the arrow A1 direction (i.e., clockwise), the R2 reagent container 110 returns to the fully sealed state. In this manner, moving the R2 reagent container 110 to the R2 reagent aspirating position P2a and provisionally opening the cover 130 of the R2 reagent container 110 can be performed in parallel, and also, moving the R2 reagent container 110 to the R2 reagent information reading/writing position P2d and sealing the R2 reagent container 110 with the cover 130 can be performed in parallel. Therefore, a time required for moving the R2 reagent container 110 between the R2 reagent aspirating position P2a and the R2 reagent information reading/writing position P2d and for opening/closing the cover 130 can be reduced.

Still further, as described above in the present embodiment, the CPU 2a is configured to perform the reagent information reading/writing process operation if it is determined that the R2 reagent has been properly aspirated by a predetermined amount. Accordingly, information is written into the IC tag 150 of the R2 reagent container 110 only when the R2 reagent has been aspirated from the R2 reagent container 110. This makes it possible to write accurate reagent information into the IC tag 150.

Still further, as described above in the present embodiment, if radio waves for writing which contain reagent information including the number of performable analyses are transmitted from an antenna to the IC tag of a reagent container and the reagent information is written into the IC tag, then the CPU 2a transmits to the control apparatus 4 the same information as the reagent information that has been written into the IC tag. Upon receiving the information, the control apparatus 4 uses the information to update the reagent information in the memory 4d. Therefore, even if reagent information cannot be written into the IC tag due to, for example, malfunction of the IC tag, the amount of reagent in the reagent container can be confirmed based on the reagent information stored in the memory 4d.

It should be noted that the embodiment disclosed herein is merely illustrative in all aspects and should not be recognized as being restrictive. The scope of the present invention is defined not by the description of the above embodiment but by the scope of the claims, and includes meaning equivalent to the scope of the claims and all modifications within the scope.

For example, the above embodiment describes an example in which the sample analyzer of the present invention is applied to the immune analyzer 1. However, the present invention is not limited thereto. The present invention is applicable to any apparatus so long as the apparatus includes a reagent aspirator for aspirating a reagent and a writer for writing reagent amount information into an information storage medium. Thus, the present invention is applicable not only to an immune analyzer but also to a blood coagulation analyzer, urine sample measurement apparatus, gene amplification detection apparatus, etc.

The above embodiment describes the number of performable analyses as the reagent amount information to be written into the IC tag. However, the present invention is not limited thereto. In the present invention, not the number of performable analyses but remaining reagent amount information may be written into the IC tag as the reagent amount information. This makes it possible to readily confirm the remaining reagent amount in the reagent container to which the IC tag is attached.

Further, the above embodiment describes an example in which the reagent provisionally opening position and the reagent sealing position are arranged between the reagent aspirating position and the reagent information reading/writing position. However, the present invention is not limited thereto. In the present invention, the opening and closing of a reagent container need not be performed at a position between the reagent aspirating position and the reagent information reading/writing position. As an alternative, the opening and closing of a reagent container may be performed at a position that is not located between the reagent aspirating position and the reagent information reading/writing position. As a further alternative, the opening and closing of a reagent container may be performed at the reagent information reading/writing position.

Still further, the above embodiment describes an example in which the CPU 2a determines, after an R2 reagent container 110 from which the R2 reagent has been aspirated is located at the R2 reagent information reading/writing position P2d, whether the R2 reagent has been properly aspirated by a predetermined amount. However, the present invention is not limited thereto. In the present invention, the CPU may determine, before the reagent container is located at the reagent information reading/writing position, whether the reagent has been properly aspirated.

Still further, the above embodiment describes an example in which the short-range antenna 21 reads and writes reagent information from and into the IC tag 150 by using radio waves, and the long-range antenna 22 reads and writes reagent information from and into the IC tag 160 by using radio waves. However, the present invention is not limited thereto. For example, such reading from and writing into an information storage medium may be performed by using magnetism.

Still further, the above embodiment describes an example in which the inner table 162 and the outer table 163 are both provided in an annular manner. However, the present invention is not limited thereto. For example, the inner table and the outer table, each of which linearly extends in a predetermined direction, may be arranged in parallel.

Still further, the above embodiment describes an example in which the two antennas, which are the short-range antenna 21 and the long-range antenna 22, are provided at the outer periphery of the outer table 163. However, the present invention is not limited thereto. In the present invention, the number of antennas may be three or more, and the antennas may be provided between the outer table and the inner table or at the inner periphery of the inner table.

Still further, the above embodiment describes an example in which the covers of reagent containers are opened and closed by utilizing the rotations of the tables 163 and 162 which are driven by the rotation drivers 163a and 162a, respectively. However, the present invention is not limited thereto. For example, a mechanism for opening and closing the covers of reagent containers may be provided separately. In such a case, the covers of reagent containers may be opened and closed without utilizing the rotations of the tables.

In the above embodiment, reagent amount information is written into the IC tag of a reagent container from which a reagent has been aspirated, and then, a reagent container that is the next reagent aspirating target is moved to the reagent aspirating position and a reagent is aspirated from the reagent container at the reagent aspirating position. However, the present invention is not limited thereto. For example, as an alternative, while an operation of writing reagent amount information into the IC tag of a reagent container from which a reagent has been aspirated is being performed at the reagent information reading/writing position, the next reagent aspirating operation may be performed on a reagent container located at the reagent aspirating position. In this case, a process of confirming whether the reagent amount information has been successfully written into the IC tag at the reagent information reading/writing position may be performed during a period until the next reagent aspirating operation ends.

Further, in the above embodiment, the liquid surface of a reagent in a reagent container is detected based on a change in electrostatic capacitance, which change is caused by a contact between the liquid surface of the reagent and a pipette, and thus the remaining reagent amount is monitored. However, the present invention is not limited thereto. For example, the remaining reagent amount may be monitored by detecting the weight of the reagent container by using a weight sensor. Alternatively, an ultrasonic oscillator may be used to transmit ultrasonic waves to the liquid surface of a reagent. The remaining reagent amount may be monitored by calculating the distance from the ultrasonic oscillator to the liquid surface of the reagent. Further alternatively, a light emitter may be used to emit light to the liquid surface of a reagent. The remaining reagent amount may be monitored by calculating the distance from the light emitter to the liquid surface of the reagent.

What is claimed is:

1. A sample analyzer for analyzing a sample by using a reagent contained in a reagent container, the sample analyzer comprising:

a reagent container holder configured to hold a reagent container to which an information storage medium is attached;

an actuator configured to actuate the reagent container holder to move the reagent container held by the reagent container holder to a first position and a second position different from the first position;

a reagent aspirator configured to aspirate a reagent from the reagent container when the reagent container is located at the first position;

an information communication section configured to write reagent amount information regarding an amount of the reagent in the reagent container, into the information storage medium attached to the reagent container when the reagent container is located at the second position; and a controller configured to control at least the actuator and the information communication section, wherein the controller is configured to control the actuator and the information communication section such that after a reagent in a first reagent container has been aspirated by the reagent aspirator and before a reagent in a second reagent container which is a next reagent aspirating target after the first reagent container is aspirated by the reagent aspirator, the first reagent container is moved from the first position to the second position and the reagent amount information is written into an information storage medium of the first reagent container.

2. The sample analyzer of claim 1, wherein
the information communication section is configured to read information stored in the information storage medium attached to the reagent container which is located at the second position, and
the controller is configured to control the actuator and the information communication section such that after the reagent in the first reagent container has been aspirated by the reagent aspirator and before the reagent in the second reagent container is aspirated by the reagent aspirator, the first reagent container is moved from the first position to the second position, and information is read from the information storage medium of the first reagent container, and the reagent amount information is written into the information storage medium of the first reagent container.

3. The sample analyzer of claim 1, wherein
if a reagent for an analysis item is aspirated following the reagent in the first reagent container and the reagent for the analysis item is the same as an analysis item for which the reagent in the first reagent container is used, the controller determines the first reagent container as the second reagent container which is the next reagent aspirating target after the first reagent container.

4. The sample analyzer of claim 1, wherein
the reagent amount information contains information indicative of a number of analyses performable within the amount of the reagent in the reagent container.

5. The sample analyzer of claim 1, wherein
the reagent amount information contains a volume of the reagent in the reagent container.

6. The sample analyzer of claim 1, further comprising a detector configured to detect a remaining amount of the reagent in the reagent container, wherein
the controller is configured to determine, based on a detection result of the detector, whether a predetermined amount of the reagent is present in the reagent container.

7. The sample analyzer of claim 6, wherein
the reagent aspirator comprises a reagent aspirating pipette configured to aspirate the reagent from the reagent container,
the detector is a liquid surface detector configured to detect a liquid surface position of the reagent in the reagent container by electrically detecting a contact between the liquid surface in the reagent container and the reagent aspirating pipette, and
the information communication section is configured to write the reagent amount information into the information storage medium via radio wave.

8. The sample analyzer of claim 1, wherein
the information storage medium is an electronic tag, and
the information communication section comprises an antenna configured to write the reagent amount information into the electronic tag via radio wave.

9. The sample analyzer of claim 1, wherein
the reagent container held by the reagent container holder comprises a cover,
the sample analyzer further comprises a cover opening mechanism configured to open the cover of the reagent container held by the reagent container holder, and
the controller is configured to control the actuator and the information communication section such that after a reagent in a first reagent container has been aspirated by the reagent aspirator and before a cover of a second reagent container which is a next reagent aspirating target after the first reagent container is opened by the cover opening mechanism, the first reagent container is moved from the first position to the second position and the reagent amount information is written into an information storage medium of the first reagent container.

10. The sample analyzer of claim 9, further comprising a contact member configured to contact the cover of the reagent container held by the reagent container holder, wherein
the cover of the reagent container is configured to be closed when the contact member and the cover of the reagent container come into contact with each other as a result of a movement of the reagent container from the first position to the second position.

11. The sample analyzer of claim 10, wherein
the cover opening mechanism and the contact member are both disposed between the first position and the second position, and
the controller is configured to:
actuate the reagent container holder to move the reagent container in a first direction from the second position toward the first position to open, by means of the cover opening mechanism, the cover of the reagent container which is a reagent aspirating target, and to move the reagent container until the reagent container arrives at the first position; and
actuate the reagent container holder to move the reagent container in a second direction opposite to the first direction from the first position toward the second position to close, by means of the contact member, the cover of the reagent container after the reagent has been aspirated from the reagent container, and to move the reagent container until the reagent container arrives at the second position.

12. The sample analyzer of claim 1, wherein
the controller is configured to:
determine whether the reagent in the reagent container has been aspirated by the reagent aspirator; and
when determining that the reagent in the reagent container has been aspirated by the reagent aspirator, control the information communication section to write the reagent amount information into the information storage medium of the reagent container.

13. The sample analyzer of claim 1, further comprising a memory, wherein
the controller is configured to store the reagent amount information in the memory when the reagent amount information is written into the information storage medium of the reagent container.

14. A reagent information writing method executed by a sample analyzer which analyzes a sample by using a reagent contained in a reagent container, the reagent information writing method comprising steps of:
moving a reagent container to a first position;
aspirating a reagent from the reagent container when the reagent container is located at the first position;
moving the reagent container to a second position different from the first position after the reagent has been aspirated from the reagent container; and
writing reagent amount information regarding an amount of the reagent in the reagent container, into an information storage medium attached to the reagent container when the reagent container is located at the second position;
aspirating a reagent from a second reagent container which is a next reagent aspirating target, after reagent amount information of a first reagent container has been written into an information storage medium of the first reagent container.

15. The reagent information writing method of claim 14, further comprising after the reagent amount information of the first reagent container has been written into the information storage medium of the first reagent container, opening a cover of a second reagent container which is a next reagent aspirating target after the first reagent container.

16. The reagent information writing method of claim 14, wherein the information storage medium is an electronic tag; and the writing step comprises writing the reagent amount information into the electronic tag via radio wave.

* * * * *